(12) United States Patent
Pavlov et al.

(10) Patent No.: US 8,865,641 B2
(45) Date of Patent: Oct. 21, 2014

(54) METHODS OF TREATMENT OF FATTY LIVER DISEASE BY PHARMACOLOGICAL ACTIVATION OF CHOLINERGIC PATHWAYS

(75) Inventors: Valentin A. Pavlov, Bayside, NY (US); Kevin J. Tracey, Old Greenwich, CT (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 162 days.

(21) Appl. No.: 13/523,519

(22) Filed: Jun. 14, 2012

(65) Prior Publication Data
US 2012/0322719 A1    Dec. 20, 2012

Related U.S. Application Data

(60) Provisional application No. 61/497,838, filed on Jun. 16, 2011.

(51) Int. Cl.
| | |
|---|---|
| A61K 38/00 | (2006.01) |
| A01N 43/00 | (2006.01) |
| A01N 43/46 | (2006.01) |
| A61K 31/55 | (2006.01) |
| A01N 43/62 | (2006.01) |
| A61K 31/4965 | (2006.01) |
| A01N 43/42 | (2006.01) |
| A61K 31/44 | (2006.01) |
| A01N 43/90 | (2006.01) |
| A01N 43/40 | (2006.01) |
| A61K 31/425 | (2006.01) |
| A01N 43/08 | (2006.01) |
| A61K 31/34 | (2006.01) |
| A01N 47/10 | (2006.01) |
| A61K 31/27 | (2006.01) |
| A01N 37/18 | (2006.01) |
| A61K 31/16 | (2006.01) |
| A01N 33/12 | (2006.01) |
| A61K 31/14 | (2006.01) |
| A61K 31/444 | (2006.01) |
| A61K 31/495 | (2006.01) |
| A61K 31/341 | (2006.01) |
| A61K 31/4545 | (2006.01) |
| A61K 31/46 | (2006.01) |
| A61K 31/5513 | (2006.01) |
| A61K 31/167 | (2006.01) |
| A61K 31/439 | (2006.01) |

(52) U.S. Cl.
CPC ........... *A61K 31/14* (2013.01); *A61K 31/444* (2013.01); *A61K 31/495* (2013.01); *A61K 31/55* (2013.01); *A61K 31/341* (2013.01); *A61K 31/27* (2013.01); *A61K 31/4545* (2013.01); *A61K 31/46* (2013.01); *A61K 31/5513* (2013.01); *A61K 31/167* (2013.01); *A61K 31/439* (2013.01)
USPC ....... 514/1.1; 514/215; 514/220; 514/255.03; 514/278; 514/304; 514/305; 514/316; 514/334; 514/471; 514/485; 514/614; 514/642

(58) Field of Classification Search
None
See application file for complete search history.

(56) References Cited

U.S. PATENT DOCUMENTS

| | | | |
|---|---|---|---|
| 6,610,713 B2 | 8/2003 | Tracey | |
| 6,838,471 B2 | 1/2005 | Tracey | |
| 7,238,715 B2 * | 7/2007 | Tracey et al. | ............... 514/334 |
| 7,273,872 B2 | 9/2007 | Tracey et al. | |
| 7,662,965 B2 | 2/2010 | Habgood et al. | |
| 7,807,696 B2 | 10/2010 | Al-Abed et al. | |
| 8,008,499 B2 | 8/2011 | Habgood et al. | |
| 2005/0125044 A1 | 6/2005 | Tracey | |
| 2007/0173495 A1 * | 7/2007 | Palani et al. | ............... 514/218 |
| 2007/0213350 A1 | 9/2007 | Tracey et al. | |
| 2009/0081314 A1 | 3/2009 | Wills | |
| 2011/0015231 A1 | 1/2011 | Al-Abed et al. | |
| 2011/0112128 A1 | 5/2011 | Tracey et al. | |
| 2011/0166148 A1 | 7/2011 | Tracey et al. | |

FOREIGN PATENT DOCUMENTS

| | | | |
|---|---|---|---|
| WO | WO 2007001975 A1 * | 1/2007 | |
| WO | WO 2008/040548 A3 | 4/2008 | |
| WO | WO 2011006066 A1 * | 1/2011 | |

OTHER PUBLICATIONS

Guyenet S "Whole Helath Source: Choline and Fatty Liver" <http://wholehealthsource.blogspot.com/2010/11/choline-and-fatty-liver.html> Accessed on the Internet Dec. 10, 2012. Published Nov. 29, 2010.*

Greenlee, W., et al., "Muscarinic agonists and antagonists in the treatment of Alzheimer's disease," *Il Farmaco* (56) pp: 247-250 (2001).

Satapathy, S.K., et al., "Galantamine Alleviates Inflammation and Other Obesity-Associated Complications in High-Fat Diet-Fed Mice," *Mol Med* 17(7-8):599-606 (Jul.-Aug. 2011).

* cited by examiner

*Primary Examiner* — Maury Audet
*Assistant Examiner* — Zachary J. Miknis
(74) *Attorney, Agent, or Firm* — Hamilton, Brook, Smith & Reynolds, PC.

(57) ABSTRACT

A method of treating a fatty liver disease in a subject. The method comprises administering to the subject an effective amount of a cholinergic pathway stimulating agent, wherein the fatty liver disease is selected from non-alcoholic fatty liver (NAFL), alcoholic fatty liver (AFL), non-alcoholic steatohepatitis (NASH), alcoholic steatohepatitis (ASH), NASH-associated liver fibrosis, ASH-associated liver fibrosis, non-alcoholic cirrhosis, and alcoholic cirrhosis.

29 Claims, 13 Drawing Sheets
(2 of 13 Drawing Sheet(s) Filed in Color)

| Product # | | D17450B | |
|---|---|---|---|
| | | gm% | kcal% |
| Protein | | 19.2 | 20 |
| Carbohydrate | | 67.3 | 70 |
| Fat | | 4.3 | 10 |
| | Total | | 100 |
| | kcal/gm | 3.85 | |

| Ingredient | gm | kcal |
|---|---|---|
| Casein, 80 Mesh | 200 | 800 |
| L-Cystine | 3 | 12 |
| Corn Starch | 315 | 1260 |
| Maltodextrin 10 | 35 | 140 |
| Sucrose | 350 | 1400 |
| Cellulose, BW200 | 50 | 0 |
| Soybean Oil | 25 | 225 |
| Lard* | 20 | 180 |
| Mineral Mix S10026 | 10 | 0 |
| DiCalcium Phosphate | 13 | 0 |
| Calcium Carbonate | 5.5 | 0 |
| Potassium Citrate, 1 H2O | 16.5 | 0 |
| Vitamin Mix V10001 | 10 | 40 |
| Choline Bitartrate | 2 | 0 |
| FD&C Yellow Dye #5 | 0.05 | 0 |
| Total | 1055.05 | 4057 |

Formulated by E. A. Ulman, Ph.D., Research Diets, Inc., 8/26/98 and 3/11/99.

*Typical analysis of cholesterol in lard = 0.95 mg/gram.
Cholesterol (mg)/4057 kcal = 19
Cholesterol (mg)/kg = 18

FIG. 1

| Product # | | D12492 |
|---|---|---|
| | gm% | kcal% |
| Protein | 26.2 | 20 |
| Carbohydrate | 26.3 | 20 |
| Fat | 34.9 | 60 |
| Total | | 100 |
| kcal/gm | 5.24 | |

| Ingredient | gm | kcal |
|---|---|---|
| Casein, 80 Mesh | 200 | 800 |
| L-Cystine | 3 | 12 |
| Corn Starch | 0 | 0 |
| Maltodextrin 10 | 125 | 500 |
| Sucrose | 68.8 | 275.2 |
| Cellulose, BW200 | 50 | 0 |
| Soybean Oil | 25 | 225 |
| Lard* | 245 | 2205 |
| Mineral Mix, S10026 | 10 | 0 |
| DiCalcium Phosphate | 13 | 0 |
| Calcium Carbonate | 5.5 | 0 |
| Potassium Citrate, 1 H2O | 16.5 | 0 |
| Vitamin Mix, V10001 | 10 | 40 |
| Choline Bitartrate | 2 | 0 |
| FD&C Blue Dye #1 | 0.05 | 0 |
| Total | 773.85 | 4057 |

Formulated by E. A. Ulman, Ph.D., Research Diets, Inc., 8/26/98 and 3/11/99.

*Typical analysis of cholesterol in lard = 0.95 mg/gram.
Cholesterol (mg)/4057 kcal = 232.8
Cholesterol (mg)/kg = 300.8

FIG. 2

Table 1. Effect of galantamine on abdominal adiposity in the context of mouse obesity

| | LFD-S | HFD-S | HFD-G |
|---|---|---|---|
| Mesenteric adipose tissue (g) | 0.07 ± 0.01 | 1.07 ± 0.12 # | 0.72 ± 0.11 #* |
| Retroperitoneal/perirenal adipose tissue (g) | 0.19 ± 0.02 | 0.99 ± 0.06 # | 0.75 ± 0.08 #* |
| Epididymal adipose tissue (g) | 0.67 ± 0.08 | 2.36 ± 0.15 # | 2.17 ± 0.18 # |

$P<0.05$ vs LFD-S; *$P<0.05$ vs HFD-S

METHODS OF TREATMENT OF FATTY LIVER DISEASE BY PHARMACOLOGICAL ACTIVATION OF CHOLINERGIC PATHWAYS

RELATED APPLICATION

This application claims the benefit of U.S. Provisional Application No. 61/497,838, filed on Jun. 16, 2011.

The entire teachings of the above application are incorporated herein by reference.

GOVERNMENT SUPPORT

This invention was made with government support under grant GM57226 awarded by the National Institutes of Health. The government has certain rights in the invention.

BACKGROUND OF THE INVENTION

Fatty liver disease is a condition characterized by excessive accumulation of lipids (fat) in liver. The build-up of fat in liver results in a range of clinical manifestations and progresses in stages. Depending on etiology, each stage can be characterized as non-alcoholic or alcoholic. The progression begins with simple fatty liver, or steatosis. This stage, generally regarded as benign, is characterized by the increased appearance of fat in the liver. Fatty liver can be characterized as non-alcoholic (NAFL) or alcoholic (AFL). The next stage of a fatty liver disease is a form of hepatitis known as steatohepatitis, characterized by further fat accumulation and liver tissue inflammation. Steatohepatitis can be non-alcoholic (NASH) or alcoholic (ASH). Both NASH and ASH can lead to the next stage of fatty liver disease, NASH-associated or ASH-associated fibrosis, respectively, which is characterized by scarring of the liver. Finally, fibrosis can progress to cirrhosis, which causes irreversible damage to the liver and is the most severe stage. Cirrhosis can be non-alcoholic or alcoholic.

Common risk factors for fatty liver disease are obesity, diabetes and drinking alcohol to excess. While the relationship between these factors is not fully understood, they can be considered triggers for progression of the disease.

People most at risk of the disorders caused by fat accumulation in a liver are those who:
- are obese
- have insulin resistance, associated with diabetes
- have hypertension (high blood pressure)
- have hyperlipidemia (too much cholesterol and triglyceride in their blood)
- are taking certain drugs prescribed for other conditions
- have been malnourished, starved or given food intravenously.

Diseases caused by fat accumulation over time should be distinguished from acute fatty liver disease, which may occur during pregnancy or with certain drugs or toxins (poisons). This condition is very rare and may lead rapidly to liver failure.

There are currently no suitable agents for treating simple fatty liver disease and its progressive stages (e.g. NASH and ASH). Therefore, there is an urgent need for the treatment of this disease.

SUMMARY OF THE INVENTION

The present invention relates to a method of treating a fatty liver disease in a subject. In particular, the method comprises administering to the subject an effective amount of a cholinergic pathway stimulating agent, wherein the fatty liver disease is selected from non-alcoholic fatty liver (NAFL), alcoholic fatty liver (AFL), non-alcoholic steatohepatitis (NASH), alcoholic steatohepatitis (ASH), NASH-associated liver fibrosis, ASH-associated liver fibrosis, non-alcoholic cirrhosis and alcoholic cirrhosis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1 is a table listing the components of a low-fat diet.

FIG. 2 is a table listing the components of a high-fat diet.

FIG. 4 shows Table 1, which provides data showing effect of galantamine on abdominal adiposity.

DETAILED DESCRIPTION OF THE INVENTION

Figure 3:
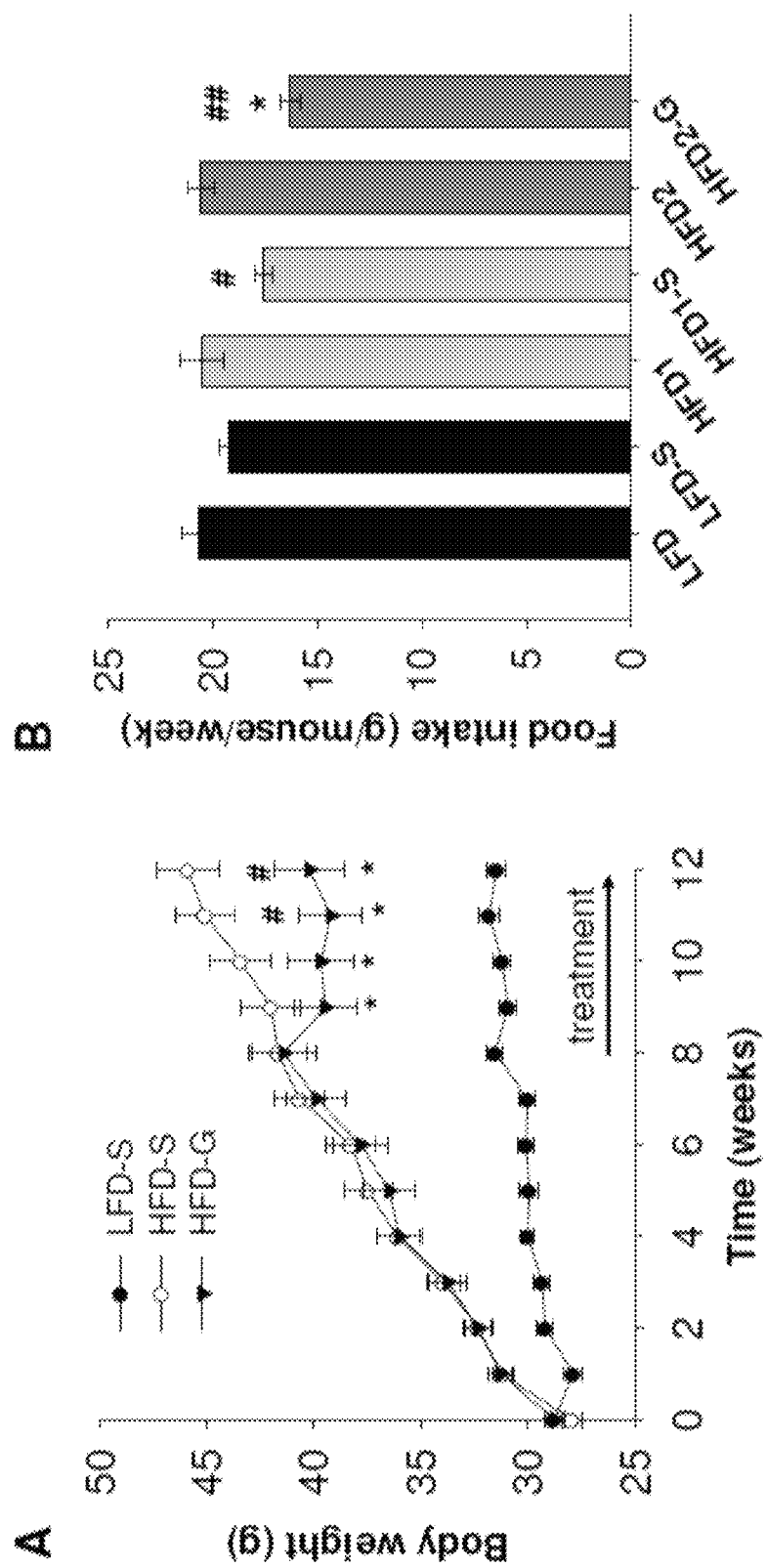
FIG. 3A is a plot showing the body weight of low-fat diet fed (control mice) and treated with saline (LFD-S), mice on a high-fat diet and treated with saline (HFD-S) and mice on a high-fat diet and treated with galantamine (HFD-G) as a function of time.
FIG. 3B is a bar graph showing the food intake of the groups of mice under study before and after treatment.

A description of example embodiments of the invention follows.

As used herein, a "cholinergic pathway" is any neural or non-neuronal pathway that includes neurons, fibers, or non-neuronal cells that employ acetylcholine as their neurotransmitter or modulator.

As used herein, a "cholinergic pathway stimulating agent" is a compound that increases signal transmission through cholinergic pathway. Examples of cholinergic pathway stimulating agents include, but are not limited to compounds that bind and activate acetylcholine receptors (nicotinic or muscarinic) to produce a desired physiological effect, i.e. "cholinergic agonists", compounds that improve signal transduction through cholinergic synapses by inhibiting activity of cholinesterase enzymes, which are the enzymes responsible for elimination of chemical neurotransmitter from the synaptic cleft, alosteric modulators that bind acetylcholine receptors and modulate/activate cholinergic transmission, muscarinic receptors antagonists that specifically bind presynaptic acetylcholine autoreceptors (e.g., M2 subtypes) and facilitate cholinergic transmission by suppressing the autoinhibition of acetylcholine release.

As used herein, an "effective amount" is defined herein as a therapeutically or prophylactically sufficient amount of the drug to achieve the desired biological effect, here, treatment or alleviation of fatty liver diseases in a subject. Examples of effective amounts typically range from about from 0.04 mg/kg of body weight to 400 mg/kg of body weight. In other examples, effective amounts range from about from 0.4 mg/kg of body weight to 40 mg/kg of body weight, or from 4 mg/kg of body weight to 20 mg/kg of body weight.

The methods of the present invention can be used to treat a fatty liver disease selected from non-alcoholic fatty liver (NAFL), alcoholic fatty liver (AFL), non-alcoholic steatohepatitis (NASH), alcoholic steatohepatitis (ASH), NASH-associated liver fibrosis, ASH-associated liver fibrosis, non-alcoholic cirrhosis, and alcoholic cirrhosis.

As used herein "treating" includes achieving, partially or substantially, one or more of the following results: partially or totally reducing the extent of the disease (e.g., reducing fat deposits, increasing insulin activity, reducing weight); ameliorating or improving a clinical symptom or indicator associated with the disorder; delaying, inhibiting or preventing the progression of the disease; or partially or totally delaying, inhibiting or preventing the onset or development of the disease. Delaying, inhibiting or preventing the progression of the disease includes for example, delaying, inhibiting or preventing the progression of normal healthy liver to simple fatty liver (either NAFL or AFL), the progression of NAFL or AFL to NASH or ASH, respectively; the progression of NASH or ASH to NASH-associated fibrosis or ASH-associated fibrosis, respectively, or the progression of NASH-associated fibrosis or ASH-associated fibrosis to non-alcoholic cirrhosis or alcoholic cirrhosis, respectively. "Treatment" also includes prophylactic treatment of subjects at risk for a fatty liver disease selected from non-alcoholic fatty liver (NAFL), alcoholic fatty liver (AFL), non-alcoholic steatohepatitis (NASH), alcoholic steatohepatitis (ASH), NASH-associated liver fibrosis, ASH-associated liver fibrosis, and non-alcoholic or alcoholic cirrhosis. "Prophylactic treatment" refers to treatment before onset of a disease to prevent, inhibit or reduce its occurrence.

As used herein, the term "subject" refers to a mammal, preferably a human, but can also mean an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like). In example embodiment, the subject is a human who does not suffer from diabetes.

The term "alkyl", as used herein, unless otherwise indicated, includes saturated monovalent hydrocarbon radicals having straight or branched moieties, typically $C_1$-$C_{10}$, preferably $C_1$-$C_6$. Examples of alkyl groups include, but are not limited to, methyl, ethyl, propyl, isopropyl, and t-butyl.

As used herein, the term "lower alkyl" refers to a $C_1$-$C_6$ alkyl.

The term "alkenyl", as used herein, unless otherwise indicated, includes alkyl moieties having at least one carbon-carbon double bond wherein alkyl is as defined above. Examples of alkenyl include, but are not limited to, ethenyl and propenyl.

The term "alkynyl", as used herein, unless otherwise indicated, includes alkyl moieties having at least one carbon-carbon triple bond wherein alkyl is as defined above. Examples of alkynyl groups include, but are not limited to, ethynyl and 2-propynyl.

The terms "alkoxy", as used herein, means an "alkyl-O—" group, wherein alkyl is as defined above.

The term "cycloalkyl", as used herein, unless otherwise indicated, includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl. "Bicycloalkyl" groups are non-aromatic saturated carbocyclic groups consisting of two rings. Examples of bicycloalkyl groups include, but are not limited to, bicyclo-[2.2.2]-octyl and norbornyl. The term "cycloalkenyl" and "bicycloalkenyl" refer to non-aromatic carbocyclic cycloalkyl and bicycloalkyl moieties as defined above, except comprising of one or more carbon-carbon double bonds connecting carbon ring members (an "endocyclic" double bond) and/or one or more carbon-carbon double bonds connecting a carbon ring member and an adjacent non-ring carbon (an "exocyclic" double bond). Examples of cycloalkenyl groups include, but are not limited to, cyclopentenyl and cyclohexenyl. A non-limiting example of a bicycloalkenyl group is norborenyl. Cycloalkyl, cycloalkenyl, bicycloalkyl, and bicycloalkenyl groups also include groups similar to those described above for each of these respective categories, but which are substituted with one or more oxo moieties. Examples of such groups with oxo moieties include, but are not limited to oxocyclopentyl, oxocyclobutyl, oxocyclopentenyl, and norcamphoryl.

The term "cycloalkoxy", as used herein, unless otherwise indicated, includes "cycloalkyl-O—" group, wherein cycloalkyl is defined above.

The term "aryl", as used herein, refers to carbocyclic group. Examples of aryl groups include, but are not limited to phenyl and naphthyl.

The term "heteroaryl", as used herein, refers to aromatic groups containing one or more heteroatoms (O, S, or N). A heteroaryl group can be monocyclic or polycyclic. The heteroaryl groups of this invention can also include ring systems substituted with one or more oxo moieties. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

The foregoing heteroaryl groups may be C-attached or N-attached (where such is possible). For instance, a group derived from pyrrole may be pyrrol-1-yl (N-attached) or pyrrol-3-yl (C-attached).

In the context of the present invention, a bicyclic carbocyclic group is a bicyclic compound holding carbon only as a ring atom. The ring structure may in particular be aromatic, saturated, or partially saturated. Examples of such compounds include, but are not limited to, indanyl, naphthalenyl, azulenyl.

In the context of the present invention, an amino group may be a primary (—$NH_2$), secondary (—$NHR_a$), or tertiary (—$NR_aR_b$), wherein $R_a$ and $R_b$ may be any of the alkyl, alkenyl, alkynyl, alkoxy, cycloalkyl, cycloalkoxy, aryl, heteroaryl, and a bicyclic carbocyclic group.

As used herein, the term "Ghy" refers to guanylhydrazone (or amidinohydrazone), i.e., NH2(CNH)—NH—N=. As used herein, the term "redGhy" refers to reduced guanylhydrazone (or reduced amidinohydrazone), i.e., NH2(CNH)—NH—NH—.

Methods of Treating a Fatty Liver Disease in a Subject

In example embodiment, the present invention is a method of treating a fatty liver disease in a subject, comprising administering to the subject an effective amount of a cholinergic pathway stimulating agent, wherein the fatty liver disease is selected from non-alcoholic fatty liver (NAFL), alcoholic fatty liver (AFL), non-alcoholic steatohepatitis (NASH), alcoholic steatohepatitis (ASH), NASH-associated liver fibrosis, ASH-associated liver fibrosis, non-alcoholic cirrhosis and alcoholic cirrhosis. For example, the fatty liver disease can be non-alcoholic fatty liver (NAFL) or alcoholic fatty liver (AFL). In another example, the fatty liver disease can be non-alcoholic steatohepatitis (NASH) or alcoholic steatohepatitis (ASH).

In example embodiments, the methods of treating a fatty liver disease described herein include administering to a subject an effective amount of one or more cholinergic pathway stimulating agent selected from the group consisting of a nicotinic receptor agonist, a muscarinic receptor agonist, a cholinesterase inhibitor and an antagonist of presynaptic acetylcholine autoreceptors.

Muscarinic Receptors Agonists

In one embodiment of the present invention, the cholinergic pathway stimulating agent is an agonist that activates a muscarinic receptor, including those in the brain. As used herein, a muscarinic agonist is a compound that can bind to and activate a muscarinic receptor to produce a desired physiological effect. The muscarinic agonist can be administered to the subject or be naturally produced in vivo.

A muscarinic receptor is a cholinergic receptor which contains a recognition site for a muscarinic agonist (such as muscarine). In an example embodiment, the muscarinic agonist is non-selective and acts on other receptors in addition to muscarinic receptors, for example, another cholinergic receptor. An example of such a muscarinic agonist is acetylcholine. In an example embodiment, the muscarinic agonist activates muscarinic receptors to a greater extent than other cholinergic receptors, for example, nicotinic receptors (for example at least 10% greater, 20% greater, 50% greater, 75% greater, 90% greater or 95% greater).

In an example embodiment the muscarinic agonist is selective for an M1, M2, or M4 muscarinic receptor (as disclosed in U.S. Pat. Nos. 6,602,891, 6,528,529, 5,726,179, 5,718,912, 5,618,818, 5,403,845, 5,175,166, 5,106,853, 5,073,560 and U.S. patent application Ser. No. 10/375,696 filed Feb. 26, 2003, the contents of each of which are incorporated herein by reference in their entirety). As used herein, an agonist that is selective for an M1, M2, or M4 receptor is an agonist that activates an M1, M2, and/or M4 receptor to a greater extent than at least one, or at least two, or at least five other muscarinic receptor subtypes (for example, M3 or M5 muscarinic receptors) and/or at least one, or at least two, or at least five other cholinergic receptors. In an example embodiment, the agonist has at least 10% greater activation activity, 20% greater activation activity, 50% greater activation activity, 75% greater activation activity, 90% greater activation activity, or 95% greater activation activity than with respect to muscarinic and/or cholinergic receptor subtypes other than M1, M2, and/or M4 receptors. Activation activity can be determined using assays known to one of skill in the art.

Nonlimiting examples of cholinergic pathway stimulating agents useful for these methods include: muscarine, McN-A-343, and MT-3. In a certain example embodiment, compounds useful for practicing the present invention are represented by structural formula (I) or a pharmaceutically acceptable salt thereof:

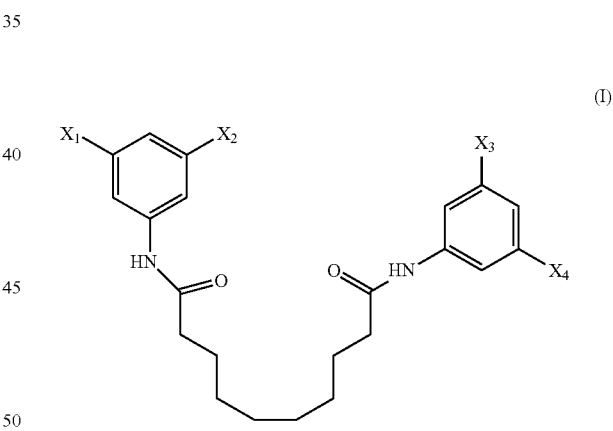

(I)

In structural formula (I), $X_1$, $X_2$, $X_3$ and $X_4$ is each independently GhyCH, GhyCCH$_3$, redGhyCH$_2$, or redGhyCHCH$_3$, or H, provided at least one of $X_1$, $X_2$, $X_3$ and $X_4$ is not H, wherein GhyCH is NH$_2$(CNH)—NH—N=CH—, GhyCCH$_3$ is NH$_2$(CNH)—NH—N=C(CH$_3$)—, redGhyCH$_2$ is NH$_2$(CNH)—NH—NH—CH$_2$— and redGhyCHCH$_3$ is NH$_2$(CNH)—NH—NH—CH(CH$_3$)—.

In a certain example embodiment, the compound of formula (I) useful for practicing the present invention is N,N'-bis(3,5-diacetylphenyl) decanediamide tetrakis (amidinohydrazone) tetrahydrochloride (CNI-1493), which has the following structural formula:

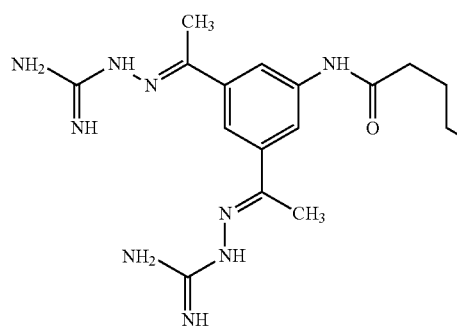 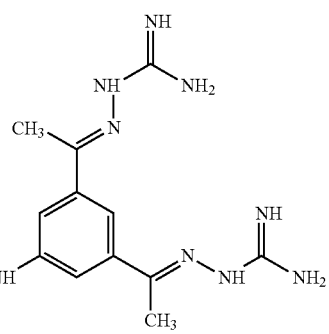

An Antagonist of Presynaptic Acetylcholine Autoreceptors

In example embodiments, cholinergic pathway stimulating agents useful for practicing the methods described herein are muscarinic receptors antagonists that specifically bind presynaptic acetylcholine autoreceptors (e.g., M2 subtypes) and facilitate cholinergic transmission by suppressing the autoinhibition of acetylcholine release.

Examples of suitable presynaptic acetylcholine autoreceptor antagonists are (BBN-99)

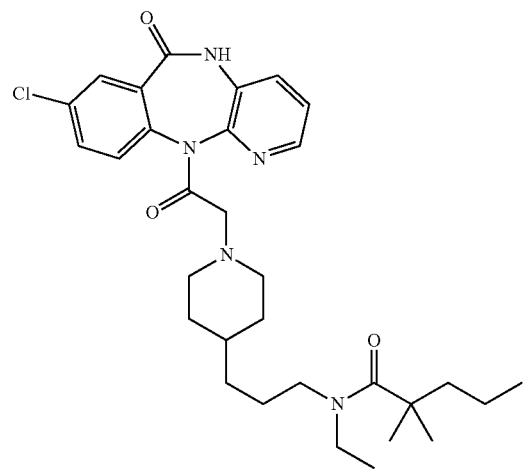

;

-continued (XX)

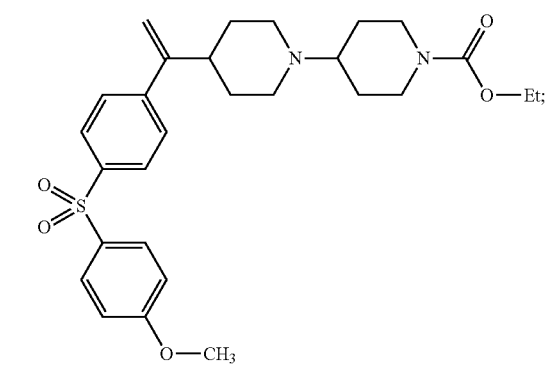

(SCH-76050)

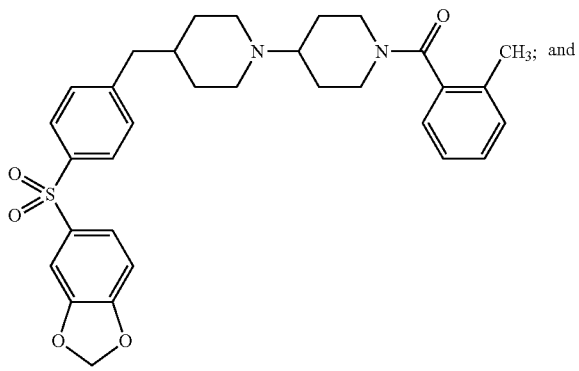

; and (SCH-217443)

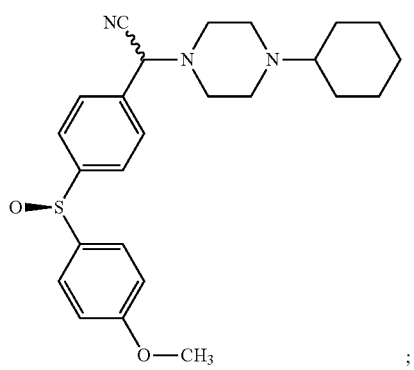

.

(SCH-57790)

Nicotinic Receptor Agonists

In one embodiment of the present invention, a cholinergic pathway stimulating agent is a nicotinic receptor agonist. The skilled artisan can determine whether any particular compound is a cholinergic agonist by any of several well known methods. The cholinergic agonist can be administered to the subject or be naturally produced in vivo. Nonlimiting examples of cholinergic agonists suitable for use in the disclosed invention include: acetylcholine, nicotine, muscarine, carbachol, galantamine, arecoline, cevimeline, and levamisole. In one embodiment the cholinergic agonist is acetylcholine, nicotine, or muscarine.

In one example embodiment, the cholinergic agonist is an α7 selective nicotinic cholinergic agonist. As used herein an α7 selective nicotinic cholinergic agonist is a compound that selectively binds to and activates an α7 nicotinic cholinergic receptor in a subject. Nicotinic cholinergic receptors are a family of ligand-gated, pentameric ion channels. In humans, 16 different subunits (α1-7, α9-10, β1-4, δ, ε, and γ) have been identified that form a large number of homo- and heteropentameric receptors with distinct structural and pharmacological properties (Lindstrom, J. M., Nicotinic Acetylcholine Receptors. In "Hand Book of Receptors and Channels: Ligand- and Voltage-Gated Ion Channels" Edited by R. Alan North CRC Press Inc., (1995); Leonard, S., & Bertrand, D., Neuronal nicotinic receptors: from structure to function. *Nicotine & Tobacco Res.* 3:203-223 (2001); Le Novere, N., & Changeux, J-P., Molecular evolution of the nicotinic acetylcholine receptor: an example of multigene family in excitable cells, *J. Mol. Evol.*, 40:155-172 (1995)).

As used herein, a cholinergic agonist is selective for an α7 nicotinic cholinergic receptor if that agonist activates an α7 nicotinic cholinergic receptor to a greater extent than the agonist activates at least one other nicotinic receptor. It is preferred that the α7 selective nicotinic agonist activates the α7 nicotinic receptor at least two-fold, at least five-fold, at least ten-fold, and most preferably at least fifty-fold more than at least one other nicotinic receptor (and preferably at least two, three, or five other nicotinic receptors). Most preferably, the α7 selective nicotinic agonist will not activate another nicotinic receptor to any measurable degree (i.e., significant at P=0.05 vs. untreated receptor in a well-controlled comparison).

Such an activation difference can be Measured by comparing activation of the various receptors by any known method, for example using an in vitro receptor binding assay, such as those produced by NovaScreen Biosciences Corporation (Hanover Md.), or by the methods disclosed in WO 02/44176 (α4β2 tested), U.S. Pat. No. 6,407,095 (peripheral nicotinic receptor of the ganglion type), U.S. Patent Application Publication No. 2002/0086871 (binding of labeled ligand to membranes prepared from GH$_4$Cl cells transfected with the receptor of interest), and WO 97/30998. References which describe methods of determining agonists that are selective for α7 receptors include: U.S. Pat. No. 5,977,144 (Table 1), WO 02/057275 (pg 41-42), and Holladay et al., Neuronal Nicotinic Acetylcholine Receptors as Targets for Drug Discovery, Journal of Medicinal Chemistry, 40:4169-4194 (1997), the teachings of these references are incorporated herein by reference in their entirety. Assays for other nicotinic receptor subtypes are known to the skilled artisan.

In one embodiment the nicotinic agonist is a compound of structural formula (III):

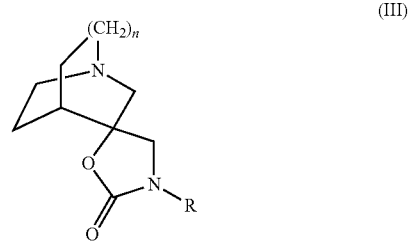

wherein:
R is hydrogen or methyl; and
n is 0 or 1; or
a pharmaceutically acceptable salt thereof.

In an example embodiment the α7 selective nicotinic agonist is (−)-spiro[1-azabicyclo[2.2.2]octane-3,5'-oxazolidin-2'-one]. Methods of preparation of compounds of structural formula III are described in U.S. Pat. No. 5,902,814, the contents of which are incorporated herein by reference in their entirety.

In another embodiment, the α7 selective nicotinic agonist is a compound of structural formula (IV):

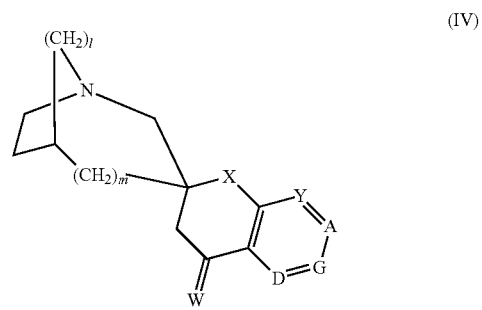

wherein:
l is 1 or 2;
m is 0 or 1;
Y is CH, N, or NO;
X is oxygen or sulfur;
W is oxygen, H$_2$, or F$_2$;
A is N or C(R$^2$);
G is N or C(R$^3$);
D is N or C(R$^4$);
R$^2$, R$^3$, and R$^4$ are independently hydrogen, halogen, C$_1$-C$_4$ alkyl, C$_2$-C$_4$ alkenyl, C$_2$-C$_4$ alkynyl, aryl, heteroaryl, OH, OC$_1$-C$_4$ alkyl, CO$_2$R$^1$, —CN, —NO$_2$, —NR$^5$R$^6$, —CF$_3$ or —OSO$_2$CF$_3$; or
R$^2$ and R$^3$, or R$^3$ and R$^4$, respectively, may together form another six membered aromatic or heteroaromatic ring sharing A and G, or G and D, respectively, containing between zero and two nitrogen atoms, and substituted with one to two of the following substitutents: independently hydrogen, halogen, C$_1$-C$_4$ alkyl, C$_2$-C$_4$ alkenyl, C$_2$-C$_4$ alkynyl, aryl, heteroaryl, OH, OC$_1$-C$_4$ alkyl, CO$_2$R$^{1'}$, —CN, —NO$_2$, —NR$^{5'}$R$^{6'}$, —CF$_3$ or —OSO$_2$CF$_3$;
R$^1$ and R$^{1'}$ are independently hydrogen or C$_1$ to C$_4$ alkyl;
R$^5$, R$^{5'}$, R$^6$ and R$^{6'}$ are independently hydrogen, C$_1$-C$_4$ alkyl, C(O)R$^7$, C(O)NHR$^8$, C(O)OR$^9$, SO$_2$R$^{10}$ or may together be (CH$_2$)$_j$Q(CH$_2$)$_k$; where Q is O, S, NR$^{11}$, or a bond;

j is 2 to 7;

k is 0 to 2; and

R$^7$, R$^8$, R$^9$, R$^{10}$, and R$^{11}$ are independently C$_1$-C$_4$, alkyl, aryl, or heteroaryl, an enantiomer thereof, or a pharmaceutically acceptable salt thereof.

In an example embodiment the α7 selective nicotinic agonist is (R)-(+5'-phenylspiro[1-aziobicyclo[2.2.2]octane-3,2' (3'H)-furo[2,3-b]pyridine]. Methods of preparation of compounds of structural formula (IV) are described in the U.S. Pat. No. 6,110,914, the contents of which are incorporated herein by reference in their entirety.

In yet another embodiment the α7 selective nicotinic agonist is a compound of structural formula (V):

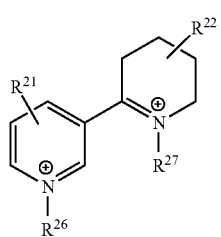

(V)

wherein:

R$^{21}$ is hydrogen or C$_1$-C$_4$ alkyl, R$^{26}$, and R$^{27}$ are independently selected from hydrogen, or C$_1$-C$_4$ alkyl or may be absent; and R$^{22}$ is:

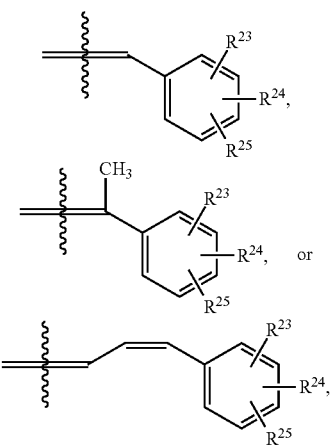

wherein:

R$^{23}$, R$^{24}$ and R$^{25}$ are independently hydrogen, C$_1$-C$_4$ alkyl optionally substituted with N,N-dialkylamino having 1 to 4 carbons in each of the alkyls, C$_1$-C$_6$ alkoxy optionally substituted with N,N-dialkylamino having 1 to 4 carbons in each of the alkyls, carboalkoxy having 1 to 4 carbons in the alkoxy, amino, amido having 1 to 4 carbons in the acyl, cyano, and N,N-dialkylamino having 1 to 4 carbons in each of the alkyls, halo, hydroxyl, or nitro.

In an example embodiment, the nicotinic agonist is:

3-(2,4-dimethoxybenzylidine)anabaseine (DMXB-A, GTS-21), 3-(4-hydroxybenzylidene)anabaseine, 3-(4-methoxybenzylidene)anabaseine, 3-(4-aminobenzylidene)anabaseine, 3-(4-hydroxy-2-methoxybenzylidene)anabaseine, 3-(4-methoxy-2-hydroxybenzylidene)anabaseine, trans-3-cinnamylidene anabaseine, trans-3-(2-methoxy-cinnamylidene)anabaseine, or trans-3-(4-methoxycinnamylidene)anabaseine.

Methods of preparation of compounds of structural formula (V) are described in U.S. Pat. Nos. 5,977,144 and 5,741,802, the contents of which are incorporated herein by reference in their entirety.

In further example embodiments, the nicotinic agonist is a compound of structural formula (VI):

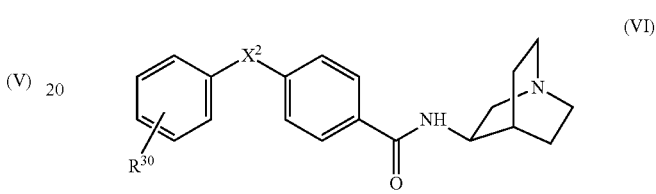

(VI)

wherein:

X$^2$ is O or S;

R$^{30}$ is H, OR$^{31}$, NHC(O)R$^{31}$, or a halogen; and

R$^{31}$ is a C$_1$-C$_4$ alkyl; or a pharmaceutically acceptable salt thereof.

In example embodiments, the nicotinic agonist is:

N-[(3R)-1-azabicyclo[2.2.2]oct-3-yl]-4-(4-hydroxyphenoxy)benzamide,

N-[(3R)-1-azabicyclo[2.2.2]oct-3-yl]-4-(4-acetamidophenoxy)benzamide,

N-[(3R)-1-azabicyclo[2.2.2]oct-3-yl]-4-(phenylsulfanyl) benzamide, or

N-[(3R)-1-azabicyclo[2.2.2]oct-3-yl]-4-(3-chlorophenylsulphonyl)benzamide.

Methods of preparation of compounds with structural formula (VI) have been described in the U.S. Patent Application 2002/0040035, the contents of which are incorporated herein by reference in their entirety.

In yet another embodiment the nicotinic agonist is (1-azabicyclo[2.2.2]oct-3-yl)-carbamic acid 1-(2-fluorophenyl)-ethyl ester. Methods of preparation of this compound have been described in the U.S. Patent Application Publication 2002/0040035, the contents of which are incorporated herein by reference in their entirety.

In another example embodiment, the nicotinic agonist is selected from: DMXB-A, 3-(4-hydroxy-2-methoxybenzylidene)anabaseine, 3-(4-hydroxy-2-methoxybenzylidene) anabaseine, (R)-(−)-5'-phenylspiro[1-azabicyclo[2.2.2]octane-3,2'octane-3,2'(3'H)-furo[2,3-b]pyridine], (−)-spiro-[1-azabicyclo[2.2.2]octane-3,5'-oxazolidin-2'-one], or cocaine methiodide.

In another example embodiment, the nicotinic agonist is selected from the group consisting of trans-3-cinnamylidene anabaseine, trans-3-(2-methoxy-cinnamylidene)anabaseine, and trans-3-(4-methoxycinnamylidene)anabaseine.

In yet another example embodiment, the nicotinic agonist is an antibody which is a selective agonist (most preferably a specific agonist) for the α7 nicotinic receptor. The antibodies can be polyclonal or monoclonal; may be from human, non-human eukaryotic, cellular, fungal or bacterial sources; may be encoded by genomic or vector-borne coding sequences; and may be elicited against native or recombinant α7 or fragments thereof with or without the use of adjuvants, all according to a variety of methods and procedures well-known in the art for generating and producing antibodies. Other examples of such useful antibodies include but are not limited to chimeric, single-chain, and various human or humanized types of antibodies, as well as various fragments thereof such as Fab fragments and fragments produced from specialized expression systems.

In additional example embodiments, the nicotinic agonist is an aptamer which is an agonist of the nicotinic receptor. Aptamers are single stranded oligonucleotides or oligonucleotide analogs that bind to a particular target molecule, such as a protein or a small molecule (e.g., a steroid or a drug, etc.). Thus aptamers are the oligonucleotide analogy to antibodies. However, aptamers are smaller than antibodies, generally in the range of 50-100 nt. Their binding is highly dependent on the secondary structure formed by the aptamer oligonucleotide. Both RNA and single stranded DNA (or analog), aptamers are known. See, e.g., Burke et al., *J. Mol. Biol.*, 264(4): 650-666 (1996); Ellington and Szostak, *Nature*, 346 (6287): 818-822 (1990); Hirao et al., *Mol. Divers.*, 4(2): 75-89 (1998); Jaeger et al., *The EMBO Journal* 17(15): 4535-4542 (1998); Kensch et al., *J. Biol. Chem.*, 275(24): 18271-18278 (2000); Schneider et al., *Biochemistry*, 34(29): 9599-9610 (1995); and U.S. Pat. Nos. 5,496,938; 5,503,978; 5,580,737; 5,654,151; 5,726,017; 5,773,598; 5,786,462; 6,028,186; 6,110,900; 6,124,449; 6,127,119; 6,140,490; 6,147,204; 6,168,778; and 6,171,795. Aptamers can also be expressed from a transfected vector (Joshi et al., *J. Virol.*, 76(13), 6545-6557 (2002)).

Aptamers that bind to virtually any particular target can be selected by using an iterative process called SELEX, which stands for Systematic Evolution of Ligands by EXponential enrichment (Burke et al., *J. Mol. Biol.*, 264(4): 650-666 (1996); Ellington and Szostak, *Nature*, 346(6287): 818-822 (1990); Schneider et al., *Biochemistry*, 34(29): 9599-9610 (1995); Tuerk et al., *Proc. Natl. Acad. Sci. USA*, 89: 6988-6992 (1992); Tuerk and Gold, *Science*, 249(4968): 505-510 (1990)). Several variations of SELEX have been developed which improve the process and allow its use under particular circumstances. See, e.g., U.S. Pat. Nos. 5,472,841; 5,503,978; 5,567,588; 5,582,981; 5,637,459; 5,683,867; 5,705,337; 5,712,375; and 6,083,696. Thus, the production of aptamers to any particular oligopeptide, including the α7 nicotinic receptor, requires no undue experimentation.

Inhibitors of Cholinesterases

A "choline esterase inhibitor" or ("cholinesterase inhibitor") is a compound that inhibits or reduces the activity of acetylcholinesterase or butyrylcholinesterase. In one embodiment, the activity of an esterase is reduced by at least 25%. In another embodiment, the activity is reduced by at least 50%. In yet another embodiment, the activity is reduced by least 75%. In another embodiment, the activity is reduced by at least 90%. In yet another embodiment, the activity is reduced by at least 99%. The activity of a cholinesterase is compared to cholinesterase activity in the absence of the compound. A "pharmaceutically acceptable" cholinesterase inhibitor is one that does not cause unacceptable side effects in the subject being treated when administered at an effective amount, as the term is defined herein. Any cholinesterase inhibitor, including inhibitors of acetylcholinesterase, of butyrylcholinesterase or dual inhibitors can be used to practice the present invention.

Examples of pharmaceutically acceptable cholinesterase inhibitors include galantamine or galantamine analogs and pharmaceutically acceptable salts thereof, tacrine or tacrine analogues and pharmaceutically acceptable salts thereof and huperzine A or its analogues and pharmaceutically acceptable salts thereof. Any of the following compounds as well as their analogs and pharmaceutically acceptable salts can be used: Green mamba snake (*Dendroaspis angusticeps*) toxin fasciculin, metrifonate, heptyl-physostigmine, norpyridostigmine, norneostigmine, physostigmine, heptyl-physostigmine, velnacrine, citicoline, donepizil, metrifonate, 7-methoxytacrine, eptastigmine, icopezil, ipidacrine, zifrosilone, anseculin, suronacrine, linopiridine, rivastigmine, physostigmine, neostigmine, edrophonium, demacarium, ambenonium and galantamine.

As used herein, tacrine refers to a compound of formula (X)

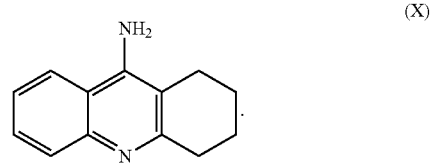 [SMILES: Nc1c2c(nc3ccccc13)CCCC2]

Tacrine and its analogs are described, for example, in U.S. Pat. Nos. 4,562,196, 4,754,050, 4,835,275, 4,839,364, 4,631,286, 4,816,456 and 6,194,403, the entire teachings of which are herein incorporated by reference.

Additionally, in the practice of the methods disclosed herein, tacrine can be replaced with a tacrine analog and derivative further disclosed in U.S. Pat. Nos. 4,562,196, 4,754,050, 4,835,275, 4,839,364, 4,631,286, 4,868,177. The entire teachings of these are herein incorporated by reference.

Additional examples of compounds suitable for practicing the present invention are disclosed in U.S. Pat. Nos. 4,550,113, 5,397,785, 5,536,728, 5,861,411 and 6,433,173, the entire teachings of which are incorporated herein by reference. Examples of these compounds include ipidacrine:

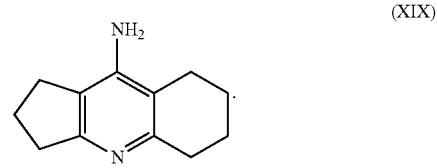 [SMILES: Nc1c2c(nc3c1CCC3)CCCC2]

As used herein, huperzine A is a compound of formula (XXII):

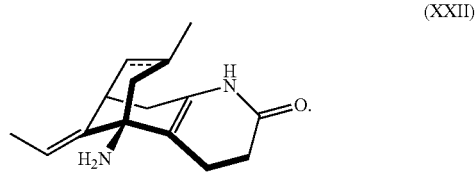

Huperzine A and its analogs are described, for example, in U.S. Pat. Nos. 5,104,880 and 5,929,084, the entire teachings of both of which are herein incorporated by reference.

As used herein, galantamine is represented by structure (XXV):

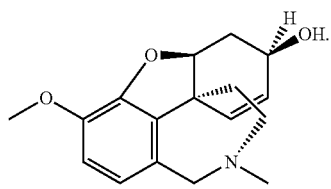

(XXV)

Galantamine derivatives included in practice of the method include metabolites of galantamine such as those shown below:

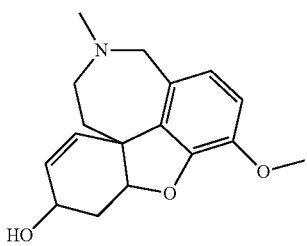

Galantamine
(unchanged drug)

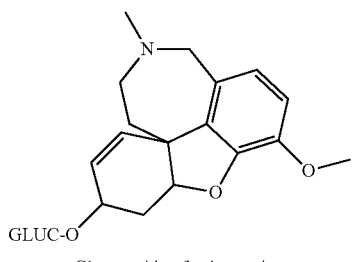

Glucuronide of galantamine

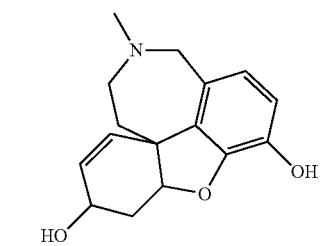

O-desmethyl-epigalantamine

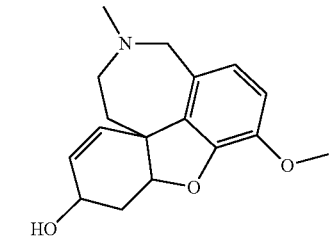

Epigalantamine

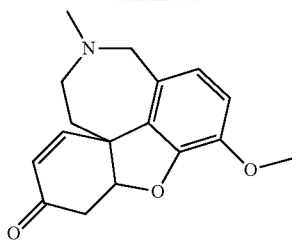

Galantaminone

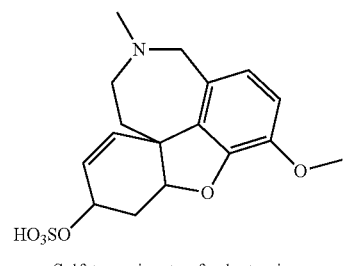

Sulfate conjugate of galantamine

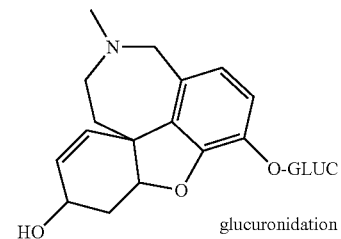

Glucuronide of O-desmethyl-galantamine glucuronidation
(R, H)

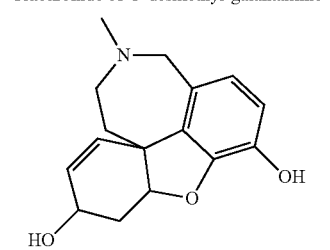

O-desmethyl-galantamine

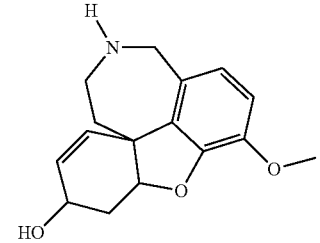

N-desmethyl-galantamine

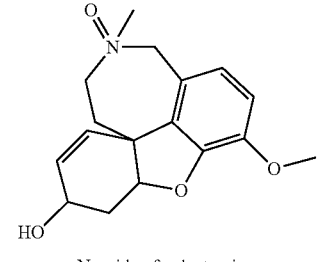

N-oxide of galantamine

-continued

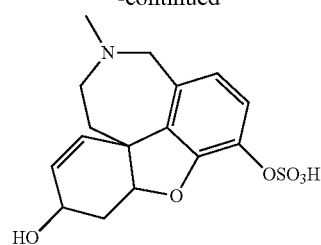
Sulfate conjugate of O-desmethyl-galantamine

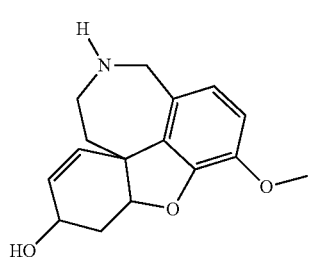
N-desmethyl-epigalantamine

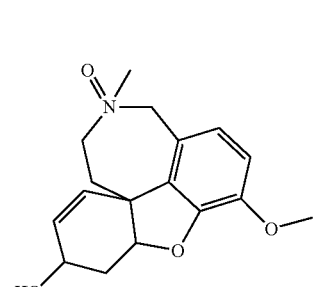
Glucuronide of O-desmethyl epigalantamine

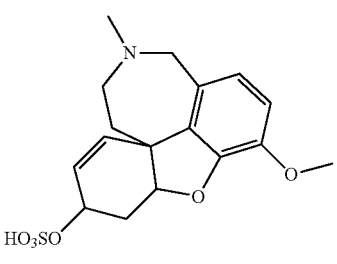
N-oxide of eipgalantamine

Sulfate conjugate of epigalantamine

-continued

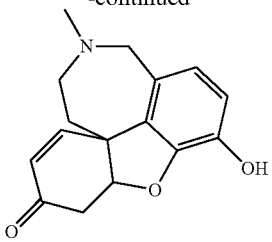
O-desmethyl-galantaminone

As used herein physostigmine is represented by formula (XXVI):

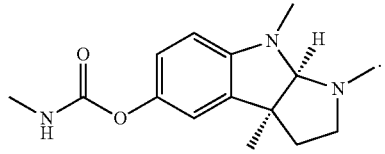
(XXVI)

In example embodiments, physostigmine can be replaced with its analogue disclosed for example in U.S. Pat. Nos. 4,831,155, 4,914,102, 4,978,155, 5,081,117, 5,306,825, disclosures of which are incorporated herein by reference in their entirety.

As used herein, rivastigmine is represented by formula

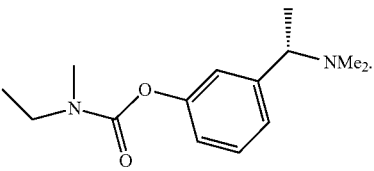
(XXXI)

Examples of derivatives of rivastigmine suitable for practicing methods disclosed herein are disclosed in U.S. Pat. No. 4,948,807, the entire teachings of which are incorporated herein by reference.

Donepezil (Aricept®), as used herein, is represented by formula (XXXIII):

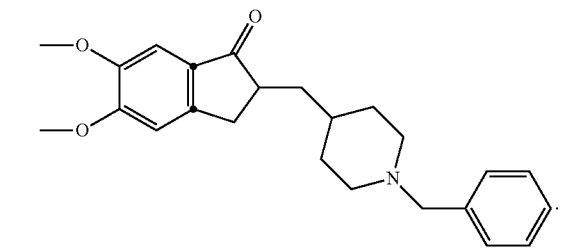
(XXXIII)

Derivatives of donepezil suitable for practicing the methods described herein are described, for example, in U.S. Pat. Nos. 4,895,841 and 5,100,901, the entire teachings of which are incorporated herein by reference.

Zifrosilone, as used herein, is represented by formula (XXXVI):

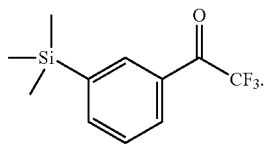
(XXXVI)

Derivatives of zifrosilone suitable for practicing the methods described herein are disclosed, for example, in U.S. Pat. Nos. 5,693,668, 5,554,780, 5,760,267, the entire teachings of which are incorporated herein by reference.

In other example embodiments, the following compounds can be used to practice the methods of the present invention: Arecoline, represented by formula (XXXVIII), Xanomeline, represented by formula (XXXIX), Subcomeline, represented by formula (XL), Cevimeline, represented by formula (XLI), Alvameline, represented by formula (XLII), Milameline, represented by formula (XLIII), or Talsaclidine, presented by formula (XLIV):

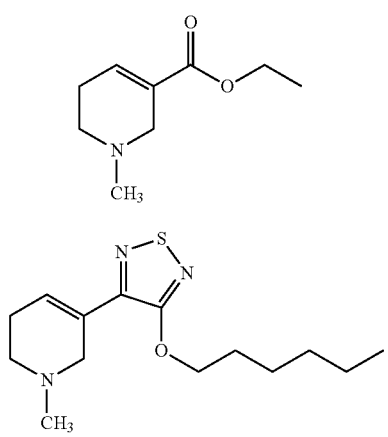
(XXXVIII)

(XXXIX)

(XL)

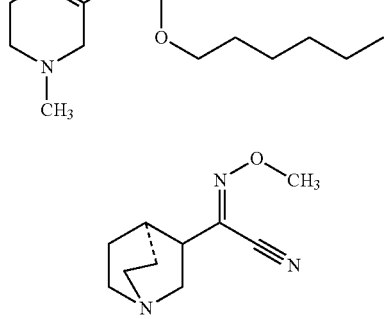
(XLI)

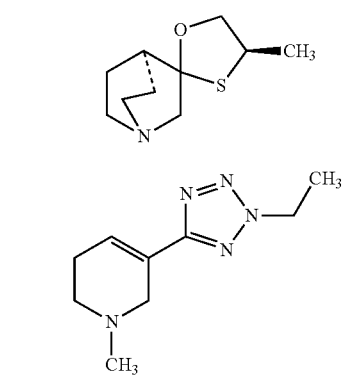
(XLII)

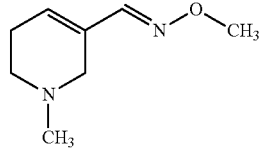
(XLIII)

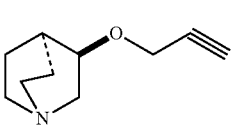
(XLIV)

In other embodiments, compounds of formulae (XLV)-(XLVIII) can be used to practice the methods of the present invention:

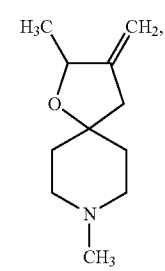
(XLV)

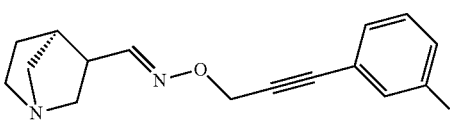
(XLVI)

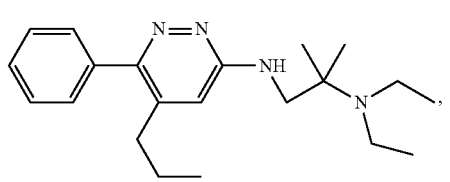
(XLVII)

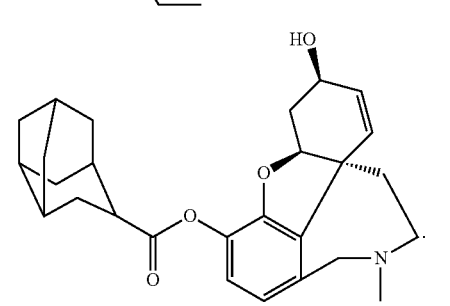
(XLVIII)

Compounds of formula (XXXVIII) through (XLVIII) are disclosed, for example, in Greenlee et al., *Il Farmaco* 56 (2001): 247-250, the entire teachings of which is incorporated herein by reference.

Pharmaceutical Compositions

As described above, the compounds can be administered in the form of a pharmaceutically acceptable salt. This includes compounds disclosed herein which possess a sufficiently acidic, a sufficiently basic, or both functional groups, and accordingly can react with any of a number of organic or inorganic bases, and organic or inorganic acids, to form a salt. Acids commonly employed to form acid addition salts from compounds with basic groups, are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, benzylphenethylamine, dehydroabietylamine, N,N'-bisdehydroabietylamine, glucamine, N-methylglucamine, collidine, quinine, quinoline, and basic amino acid such as lysine and arginine. These salts may be prepared by methods known to those skilled in the art.

The route of administration and the dosage of the compounds disclosed herein can be determined by a skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. Thus, depending on the condition, the cholinesterase inhibitor can be administered orally, parenterally, intranasally, vaginally, rectally, lingually, sublingually, bucally, and intrabuccaly to the patient.

Pharmaceutical compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

Pharmaceutical compositions described herein can easily be administered parenterally such as for example, by intravenous, intramuscular, intrathecal or subcutaneous injection. Parenteral administration can be accomplished by incorporating the cholinergic agonist compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

The compounds disclosed herein can be administered alone (as a monotherapy) or in combination with one or more other pharmaceutically active agents that are effective against the condition being treated. For example, they can be administered in combination with insulin sensitizing agents, such as metformin, statins, antioxidants, or non-steroidal anti-inflammatory agents.

Testing Efficacy of the Compounds Described Herein for Treating Non-alcoholic Hepatitis (NASH)

The following method can be used to test the compounds disclosed herein, such as galantamine, for treating NASH.

Pro-inflammatory cytokines and insulin resistance play a central role in the pathogenesis of NASH, an inflammatory liver condition histologically characterized by hepatic steatosis, inflammation, cytologic ballooning with or without fibrosis and has potential to progress to cirrhosis.

Non alcoholic fatty liver (NAFL) has become the most common liver condition worldwide, affecting 15-30% of western and eastern populations. It is histologically characterized by the presence of macrovesicular steatosis, and it occurs in the absence of excessive alcohol consumption. Its histologic spectrum includes simple steatosis and non-alcoholic steatohepatitis (NASH). The latter presentation can progress to cirrhosis in 15% to 20% of patients over the ensuing 10 to 15 years. In addition, NAFL is present in approximately one-third of the subjects with metabolic syndrome (MetS). MetS is associated with an increased risk of vascular disease, which is the leading cause of death in patients with NAFL. Statins, fibrates, anti oxidants, insulin sensitizing agents like metformin, pioglitazone, cytoprotective agents like UDCA have been tried in the therapy of NASH with some success, by improving aminotransferases, and in some cases histology; however, none of these can be recommended as the therapy for NASH as of yet. However, most of the studies are small, non-randomised and do not have any histological follow up. Thus rational approaches to halt the disease progression and reverse its associated metabolic complications are urgently needed.

The liver plays a central role in lipid metabolism, importing serum free fatty acids and manufacturing, storing and exporting lipids and lipoproteins. An imbalance between the enzyme systems that promote the uptake and synthesis of fatty acids and those that promote the oxidation and export of fatty acids leads to excess accumulation of lipids mostly in the form of triglycerides within the hepatocytes. Among the many factors incriminated in such imbalances; constitutive elevation of de novo lipogenesis, inadequate hepatic VLDL secretion, and dysfunctional VLDL synthesis are of prime importance. The progression of NAFL to NASH is a complex process. Many adipokines, such as tumor necrosis factor-alfa (TNF), leptin and resistin induce insulin resistance and a low grade inflammation in the liver. Besides, leptin, TNF-α and IL-6 also promote hepatic fibrogenesis through hepatic stellate cells (HSC) activation. Adiponectin, another adipokine, inhibits liver TNF expression, and also inhibits expression of several cytokines in hepatic stellate cells (HSC). Plasma adiponectin was significantly lower in NAFL patients than controls, possibly contributing to unregulated cytokine expression and inflammation in the liver in those developing NASH from NAFL.

Another key player in the pathogenesis of NASH is mitochondrial dysfunction that not only impairs fat homeostasis in the liver but also leads to overproduction of reactive oxygen species (ROS) that trigger lipid peroxidation, expression of several cytokines, including transforming growth factor-β (TGF-β), interleukin-8 (IL-8), TNF and Fas ligand. The net effect is neutrophil infiltration, polymerization intracellular cytokeratins, leading to formation of Mallory bodies and hepatic fibrosis.

Members of the microsomal cytochrome P-450 participate in the generation of oxidative changes in fatty livers via increased production of the free oxygen radical $H_2O_2$. Over expression of CYP2E1 in the liver has been demonstrated in both animal models and in patients with NASH. Increased hepatocyte CYP2E1 expression result in the down-regulation of insulin signaling, potentially contributing to the insulin resistance associated with non-alcoholic fatty liver. In addition, defective states of PPAR-α or of the peroxisomal β-oxidation pathway have been implicated to play an important role in the development of steatohepatitis as well.

Study Design

This study is designed to explore the efficacy of Galantamine, an AChE inhibitor with potential to improve insulin resistance, serum inflammatory markers and steatohepatitis associated with NASH. The study will focus on adults without diabetes who have NASH. Adults with diabetes will be excluded because it is unclear whether they would have the same responses to therapy as would adults without diabetes and because it was possible that changes in antidiabetic therapy might confound the analysis of data both from subjects with diabetes and from those without diabetes. All subjects will undergo a liver biopsy within 6 months before randomization.

Diagnosis of NASH:

Diagnosis of NASH will be based on histology of liver biopsy specimen using the NAFL activity score as described in Kleiner et al. Nonalcoholic Steatohepatitis Clinical Research Network. Design and validation of a histological scoring system for nonalcoholic fatty liver. Hepatology. 2005; 41:1313-21, the relevant teachings of which are incorporated herein by reference. Steatohepatitis will be categorized as absent, possible, or definite. Disease activity will be assessed with the use of the nonalcoholic fatty liver activity score, which is based on a standardized grading system for steatosis (on a scale of 0 to 3), lobular inflammation (on a scale of 0 to 3), and hepatocellular ballooning (on a scale of 0 to 2), with higher scores indicating increasing severity). The specific inclusion criteria will be definite steatohepatitis with an activity score of 4. A score of at least 1 for hepatocellular ballooning will be required in all cases. Details of the inclusion and exclusion criteria is further discussed else where in the current protocol.

Subjects who will meet the eligibility criteria and will consent to participate in the trial will be included. A total of 30 patients will be included in the current clinical trials. A 2:1 randomization scheme (galantamine:placebo) of 20 subjects in galantamine and 10 in placebo will be utilized. Galantamine Hbr (Razadyne® ER, Ortho-McNeil-Janssen Pharmaceuticals) will be administered at 8 mg/day PO, once daily for 1 month and than the dose will be escalated to 16 mg for the rest 11 month period. This dosage is FDA approved for the treating Alzheimer's disease. Patients will be followed up at the GCRC (General clinical Research Center) at 1, 2, and every 3 month interval initially, and subsequently at 3 month intervals until the conclusion of the study. Details of the follow up plan, clinical data to be collected at the contact points and tests to be performed are described below.

Pre intervention: Pre-intervention/initial screening includes blood pressure, waist and hip circumference, height, weight measurements. The following laboratory investigations will be done at the baseline: Hemogram, serum aminotransferases, total proteins, albumin, alkaline phosphatase, gamma glutamyl transferase, and total bilrubin, hepatitis B serology (HBsAg, anti-HBe), anti-HCV or undetectable HCV-RNA by RT-PCR, auto-antibodies (antinuclear antibody, anti-smooth muscle antibody, anti mitochondrial antibody); iron profile (serum iron, transferrin saturation and ferritin), ceruloplasmin, fasting serum cholesterol, triglycerides. These studies are routine and are part of standard of care in the evaluation of patients with suspected NASH, the cost of these investigation will be accrued to the patient's insurance. No routine tests which are experimental in nature will be levied to the investigators. Oral glucose tolerance test will be done with standard dose of 1.75 grams of glucose per kilogram of body weight, to a maximum dose of 75 g glucose load at the baseline. Blood glucose measurement will be done at 0, 30, 60, 90 and 120 minutes. Insulin resistance (IR) will be evaluated from fasting glucose and insulin using the Homeostasis Model Assessment of IR (HOMA IR) and the quantitative Insulin sensitivity Check Index (QUICKI), [51] and defined as HOMA IR≥2.5 or QUICKI≤0.333. Serum sample will be collected for measurement of adipokine and cytokines (TNF, IL-6, adipokines and cytokines,), markers of oxidative stress (ie. thiobarbituric acid reactive substances [TBARS]—measure of lipid peroxidation), serum markers of liver fibrosis (i.e. hyaluronic acid and procollagen III N-peptide [P-II-INP]). An abdominal ultrasound will be performed to assess the liver parenchyma, biliary tree, vascular patency, and presence of ascites or portal hypertension and also to exclude the possibility of hepatocellular carcinoma.

During study monitoring: Following parameters will be measured during the course of the study at 1, 2 and than at every 3 month intervals until the conclusion of the study: blood pressure, weight, height, waist and hip circumference, fasting serum triglycerides, HDL, fasting serum glucose, serum insulin and liver function tests.

Post-study assessment: Following parameters will be measured at the conclusion of the study. Hemogram, serum aminotransferases, total proteins, albumin, alkaline phosphatase, gamma glutamyl transferase, and total bilrubin, iron profile (serum iron, transferrin saturation and ferritin), fasting serum cholesterol, triglycerides, glucose tolerance test. Insulin resistance (IR) using the Homeostasis Model Assessment of IR (HOMA IR) and the quantitative Insulin sensitivity Check Index (QUICKI). Serum sample will be collected again for measurement of adipokine/cytokines (TNF, IL-6, adiponectin, resistin and leptin), markers of oxidative stress (ie. thiobarbituric acid reactive substances [TBARS]—measure of lipid peroxidation), serum markers of liver fibrosis (i.e. hyaluronic acid and procollagen III N-peptide [P-IIINP]).

A repeat liver biopsy will be performed in all patients enrolled in the study after obtain a written and informed consent. Liver histology will be analyzed by a single liver pathologist.

Expected results and interpretation: Plasma levels of pro-inflammatory cytokines, such as TNF, and IL-6 are elevated in patients with NASH (compared to healthy controls), associated with the chronic inflammatory state characterizing the disease. This study will investigate the efficacy of galantamine in NASH. Cholinergic enhancement by galantamine is expected to result in suppression of the inflammatory state and improved serum markers of inflammation in liver and will improve the liver histology.

Inflammatory markers in serum: Blood samples for serum cytokine measurements will be collected in 5 ml tubes (Vacutainer, Becton Dickinson, N.J., USA). Blood will be allowed to clot for 45 min at room temperature and serum will be separated by centrifugation at 5000 rpm for 10 min. The serum will be collected from subjects and stored in aliquots at −20° C. Frozen serum samples will be kept in the laboratory of Biomedical Sciences at the Feinstein Institute for Medical Research for measuring cytokines and adipokine levels using commercially available kits.

Duration of the study: The study will continue for 12 months. This is a pilot study examining changes in markers of inflammation in the liver and improvement in liver histology in subjects with NASH undergoing cholinergic enhancement. The sample size is based on feasibility and availability of resources, rather than on a formal power calculation.

EXEMPLIFICATION

Example 1

Treatment with Galantamine

The possibility of using galantamine to alleviate chronic inflammation and other obesity-associated pathologies, including hepatic steatosis, was explored in mice. High-fat diet-induced obesity was accompanied by abdominal adiposity, liver enlargement, higher plasma IL-6, leptin, resistin, hepatic alanine aminotransferase (ALT) and cholesterol levels, lower adiponectin levels, hyperglycemia, hyperinsulinemia, insulin resistance, and significantly increased hepatic steatosis on histopathology. Galantamine treatment of obese mice resulted in significantly reduced body weight, and selectively reduced abdominal adiposity and liver weight. Galantamine treatment also was associated with significantly lower plasma levels of cytokines and adipokines, including IL-6, leptin, resistin and MCP-1 as well as significant improvements of blood glucose, hyperinsulinemia, insulin sensitivity, glucose tolerance and plasma cholesterol. Hepatic aminotransferases, liver weight and hepatic steatosis were significantly decreased as a result of galantamine treatment.

The effect of galantamine administration on alleviation of obesity-related pathologies, such as a fatty liver disease, was tested. Galantamine treatment significantly reduced hepatic aminotransferases, liver weight and hepatic steatosis. In addition, galantamine reduced the inflammatory state, decreased body weight and abdominal adiposity, and alleviated insulin resistance and fatty liver in mice with high-fat diet-induced obesity.

Material and Methods
Animals

Experiments with male C57BL/6J mice (5-6 month old, Jackson Lab) were performed in accordance with the NIH Guidelines under protocols approved by the IACUC Committee of the Feinstein Institute for Medical Research, North Shore-LIJ Health System, Manhasset, N.Y., USA.

Experimental Design

C57BL/6J mice were initially fed a regular chow for 10 days and then switched to a high-fat diet (D12492, 60% kcal from fat, shown in FIG. 2) or its corresponding low-fat control diet (D12450B, 10% kcal from fat, shown in FIG. 1) (Research Diets, New Brunswick, N.J.) for 12 weeks. After the first 8 weeks mice on the high-fat diet were divided into 2 groups and treated with saline (i.p. once daily) or galantamine (Galanthamine Hydrobromide, EMD Biosciences, Inc., La Jolla, Calif., USA) (4 mg/kg, i.p., once daily) for the remaining 4 weeks of the study. In parallel, mice on the low-fat (control) diet were treated with saline. Body weight and food intake were determined on a weekly basis by trained personnel of the Center for Comparative Physiology at the Feinstein Institute, who were blinded to treatment groups. At the end of the experimental time period mice were euthanized and abdominal adiposity, liver weight, cytokine and adipokine levels, metabolic profile, insulin resistance, and liver histology were evaluated. In a separate experiment, groups of mice were fed and treated and body weights and food intake recorded as described above. At the end of the experimental time period mice were subjected to the insulin sensitivity test or the glucose tolerance test as described below.

Blood Glucose Determination

Blood glucose during the study was measured by nicking the tails and using the Contour blood glucose meter (Bayer, Elkhart, Ind.) with Contour blood glucose test strips according to the manufacturer's recommendations. After blood collection the cuts were compressed with sterile gauze until bleeding termination.

Blood Collection and Tissue Harvesting

After an overnight fast and following body weight and blood glucose determination mice were euthanized by CO2 asphyxiation. Heparinized blood was obtained by cardiac puncture and centrifuged within 30 min at 5,000 rpm for 10 min. Visceral adipose tissues and liver were harvested, rinsed with saline, and weighed. One piece of liver (the biggest lobe) was fixed in formalin for further H&E staining. Plasma and visceral fats (were frozen on dry ice) were transferred at −20° C. prior to further manipulations.

Plasma Adipokine Determination and Other Blood Biochemistry Tests

Plasma samples were sent to Millipore and plasma insulin, leptin, MCP-1, PAI-1, resistin, TNF and IL-6 levels were determined by using the Millipore's MILLIPLEX map mouse adipokine panel assay with the following detection sensitivity limits: leptin 16.71 pg/mL; resistin 1.79 pg/mL; IL-6 1.89 pg/mL; TNF 4.39 pg/mL; MCP-1 14.4 pg/mL; PAI-1 16.4 pg/mL, insulin 42.2 pg/mL. Plasma samples were sent to IDEXX and plasma levels of total cholesterol and ALT were determined by using IDEXX's Olympus analyzers and spectrophotometric determination. Plasma adiponectin was measured by using the mouse adiponectin/Acrp30 immunoassay (R&D Systems) according to the manufacturer's recommendations.

Insulin Resistance Evaluation:

Insulin resistance was evaluated by using glucose and insulin level values and by applying the homeostatic model assessment-insulin resistance (HOMA-IR) formula, presented in Mlinar et al. (2007) Molecular mechanisms of insulin resistance and associated diseases. Clin Chim Acta 375: 20-35, the relevant teachings of which is incorporated herein by reference. Specifically, the expression used to evaluate insulin resistance is:

HOMA index=insulin (mU/L)×[glucose (mmol/L)/ 22.5]

Liver Histology and Hepatic Steatosis Assessment

Formalin fixed liver tissue was imbedded in paraffin, sliced and then liver tissue sections were subjected to hematoxylin and eosin (H&E) staining and microscopic slides prepared. Hepatic steatosis was determined by microscopic evaluation of H&E stained liver sections for lipid accumulation by using Zeiss apotome and semi-quantified by applying a previously implemented grading criteria: no fat accumulation (grade 0); less than 33% fat-containing hepatocytes (grade 1); less than 66% fat-containing hepatocytes (grade 2); more than 66% fat-containing hepatocytes (grade 3).

Insulin Sensitivity and Glucose Tolerance Tests

Separate groups of mice were fed and treated and body weights and food intake recorded as described above (in Experimental design). At the end of the 12 week period, mice from the three experimental groups were used in the insulin sensitivity and glucose tolerance tests. In the insulin sensitivity test, after an overnight (18 hours) fast, mice (n=10 per group) were weighed and administered i.p. with insulin (Humulin R, Lilly, 0.5 units/kg). In the glucose tolerance test, after an overnight (21 hours) fast, mice (n=10 per group) were weighed and injected i.p. with glucose (10% D glucose solution, Sigma, 1 g/kg). Glucose levels were determined at 0, 15, 30, 60, and 120 min after insulin or glucose administration in blood from the tail vein by using the Contour blood glucose meter (Bayer, Elkhart, Ind.) with Contour blood glucose test strips.

Statistical Analysis

Data are expressed as mean±SEM. Significant differences were assessed by using one way analysis of variance (ANOVA) for multiple comparisons followed by the Bonferroni pot-hoc test. Differences with $P<0.05$ were considered statistically significant.

Results

Galantamine Suppresses Fatty Liver Manifestations in High-fat Diet-fed Mice

Figures 7A, 7B:
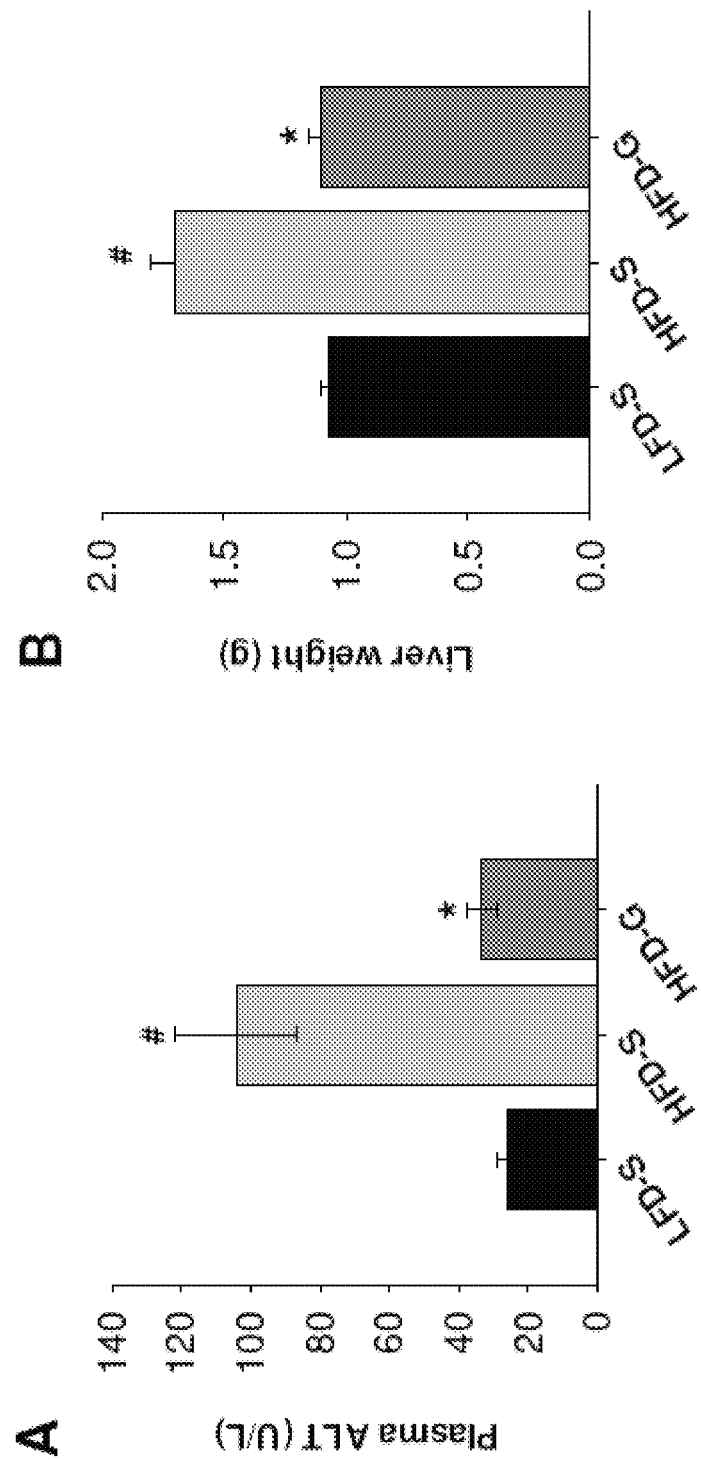
FIG. 7A and FIG. 7B are bar plots showing plasma ALT level and liver weight, respectively, in mice under study.
Figure 8:
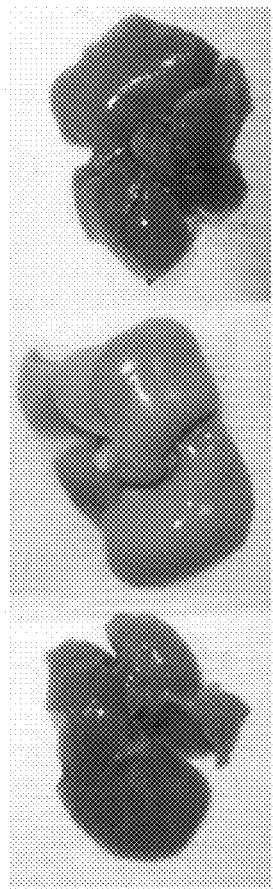
FIG. 8 is a photograph showing liver gross appearance in the three groups of mice.
Figure 9:
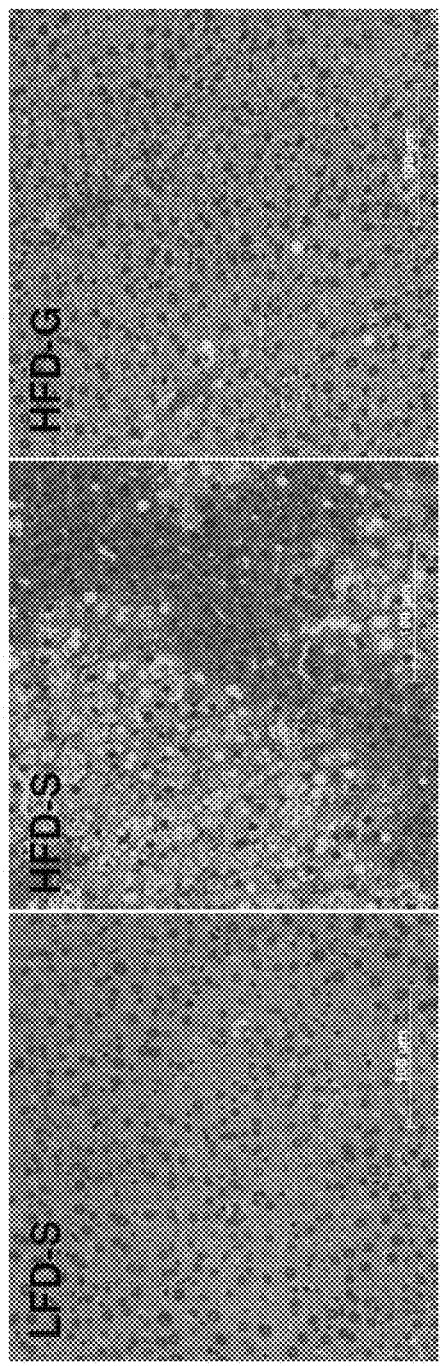
FIG. 9 is a set of three microphotographs of liver tissue of mice under study demonstrating increased hepatocyte fat accumulation (steatosis) in HFD-S mice, as compared to LFD-S mice, and that galantamine decreased lipid accumulation in HFD-G mice
Figure 10:
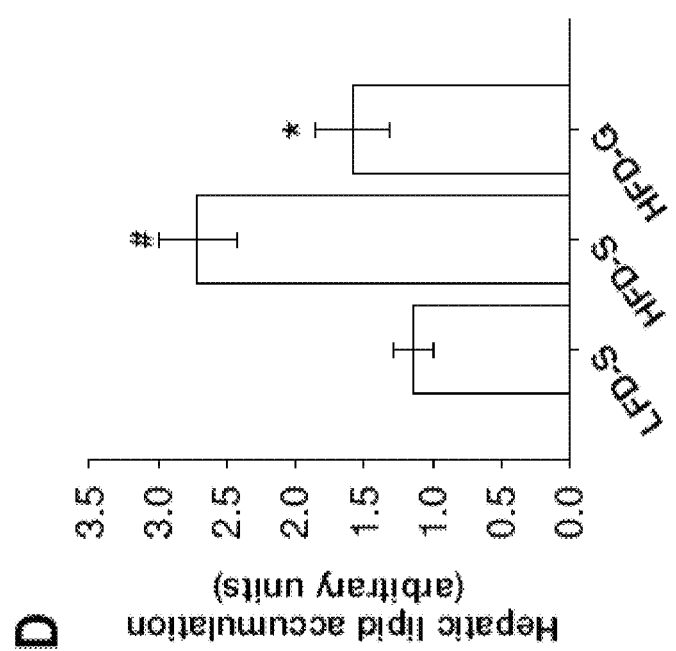
FIG. 10 is a bar plot showing lipid accumulation in livers of mice under study.

Increased plasma aminotransferase levels and lipid accumulation in the liver, are associated with a fatty liver disease. This ectopic lipid accumulation contributes to insulin resistance, dyslipidemia and insulinemia. At the end of the 12 week study time period plasma alanine aminotransferase (ALT) levels were significantly elevated in the HFD-S mice as compared to the LFD-S mice and galantamine significantly decreased ALT levels (in HFD-G mice) (FIG. 7A). These alterations were consistent with an increased liver weight in the high-fat diet-fed (HFD-S) mice, as compared to the low-fat diet-fed (LFD-S) animals, and a significant liver weight decrease following galantamine treatment (in the HFD-G mice) (FIG. 7B). The fluctuations in liver weight were associated with notable differences in liver gross appearance in the three groups of mice (FIG. 8). Microscopic observations demonstrated increased hepatocyte fat accumulation (steatosis) in HFD-S mice, as compared to LFD-S mice, and that galantamine decreased lipid accumulation in HFD-G mice (FIG. 9). Semi-quantitative analysis revealed that lipid accumulation in livers from galantamine-treated (HFD-G) mice was significantly reduced as compared to the HFD-S mice (FIG. 10). These observations indicate that galantamine alleviates fatty liver in high-fat diet-induced obesity.

Galantamine Reduces Body Weight Gain, Food Intake and Abdominal Adiposity in High-fat Diet-fed Mice To study the therapeutic efficacy of galantamine in the context of obesity, mice were fed a high-fat diet for 8 weeks prior to drug treatment. The high-fat diet for 8 weeks resulted in a gradual body weight increase that reached a difference of 10 g (P<0.05) as compared to the body weigh of control, low-fat diet-fed mice (FIG. 3A). High-fat diet-fed mice were then divided into two groups with equal average body weight and blood glucose levels (after 6 hour fast) of 229.7±11.3 mg/dl and 222.12±9.79 mg/dl, respectively, for treatment with either galantamine or vehicle (saline, i.p.) daily for 4 weeks. In parallel, after 8 weeks on a low-fat diet, mice (with an average blood glucose level of 175±6.8 mg/dl) were treated with saline (one i.p. daily injection) for 4 weeks. As shown in FIG. 3A, mice on the high-fat diet and treated with saline (HFD-S) continued gaining weight. In contrast, the weight of mice on the high-fat diet and treated with galantamine (HFD-G) was lower after the first week of treatment (at week 9 as compared to week 8) and then sustained until the end of the investigative time period. At weeks 11 and 12 the weight of HFD-G mice was lower than the weight of HFD-S mice. The weight of mice on the low-fat diet and treated with saline was not significantly altered during these 4 weeks. Food intake, which did not differ significantly among the groups of mice for the first 8 weeks preceding treatment, was reduced during treatment (FIG. 3B). Moreover, galantamine treatment was associated with additional suppression of food intake in the HFD-G group as compared to the HFD-S group (FIG. 3B). Mice on the high-fat diet (HFD-S) had increased abdominal adiposity as compared to mice on the low-fat diet (LFD-S) (Table 1, shown in FIG. 4). Galantamine treatment significantly reduced mesenteric and retroperitoneal/perirenal adipose tissue weight (HFD-G group, FIG. 4). Together these results demonstrate a sustained suppressive effect of galantamine on body weight gain during high fat diet-induced obesity, accompanied by decreased food intake, and associated with selectively reduced abdominal adipose tissue accumulation.

Galantamine Alters Systemic Cytokine/Adipokine Levels in High-Fat Diet Fed Mice

Figure 5:
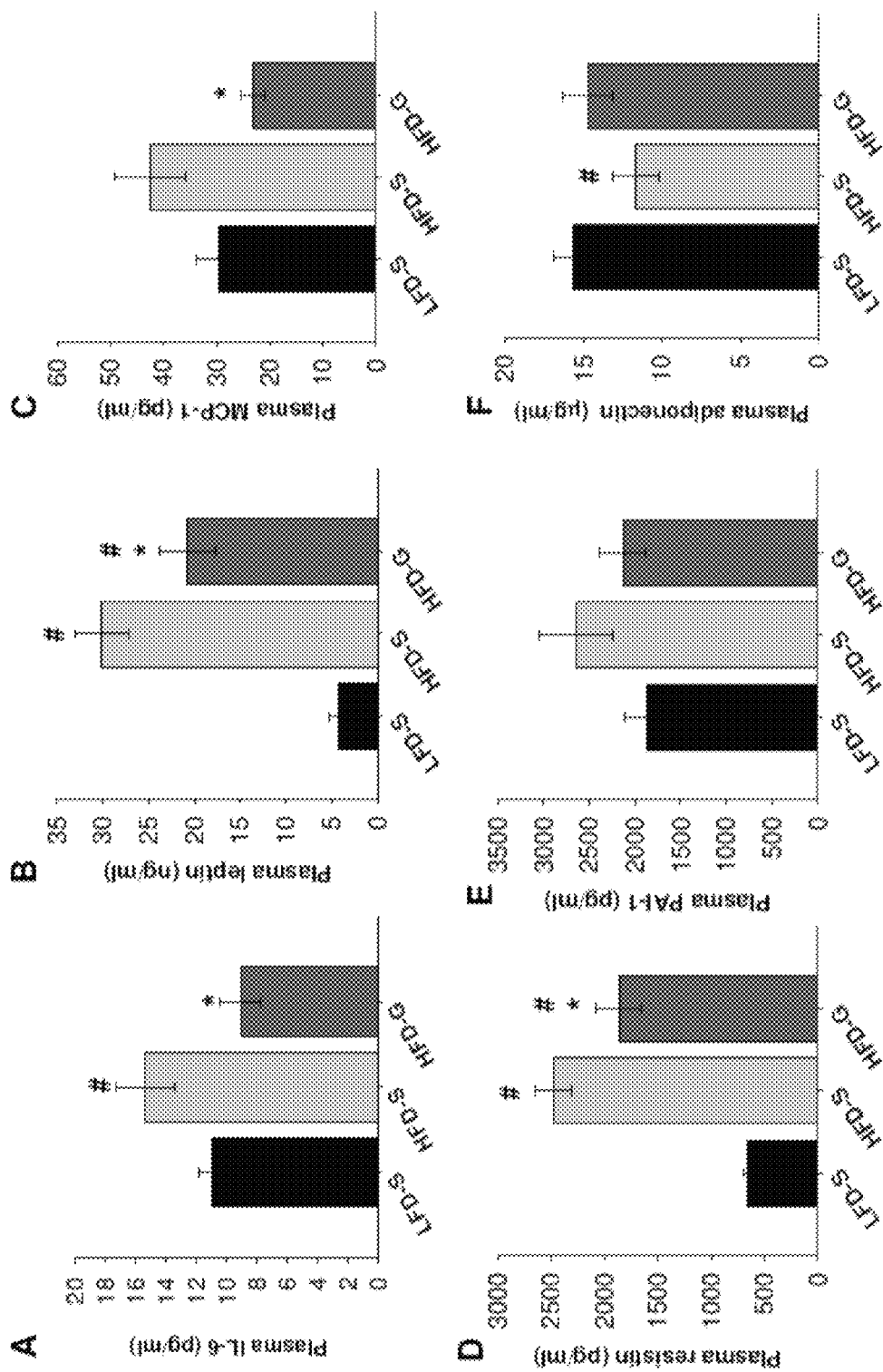
FIG. 5A through 5F are bar plots showing the measured levels of the indicated analytes in the bloodstream of mice under study.

Plasma IL-6 and leptin levels were significantly elevated in the HFD-S mice as compared to the LFD-S mice (FIG. 5A and FIG. 5B). Galantamine significantly reduced these levels (in the HFD-G mice) (FIG. 5A and FIG. 5B). Plasma MCP-1 levels were elevated (not statistically significant) in the HFD-S mice as compared to the LFD-S mice and galantamine significantly reduced MCP-1 levels in the HFD-G mice (FIG. 5C). Plasma resistin levels were significantly higher in the HFD-S mice as compared to the LFD-S mice and galantamine significantly lowered these levels in the HFD-G animals (FIG. 5D). Plasma plasminogen activator inhibitor-1 (PAI-1) levels were higher in the HFD-S mice as compared to the LFD-S and HFD-G mice, but none of these differences were statistically significant (FIG. 5E). Plasma TNF levels were under the sensitivity limit (4.39 pg/ml) of the assay used; only one value in the LFD-S group, 2 values in the HFD-S group and none in the HFD-G group above this limit were detected. Adiponectin levels have been previously shown to be negatively correlated with obesity and insulin resistance, and experimental evidence points to its anti-inflammatory function. As shown in FIG. 5F, plasma adiponectin levels were lower in the HFD-S mice as compared to LFD-S mice. Galantamine treatment resulted in a certain increase in these levels (FIG. 5F). Together these data reveal that galantamine inhibits pro-inflammatory cytokines and adipokines implicated in the development of insulin resistance.

Figure 6:
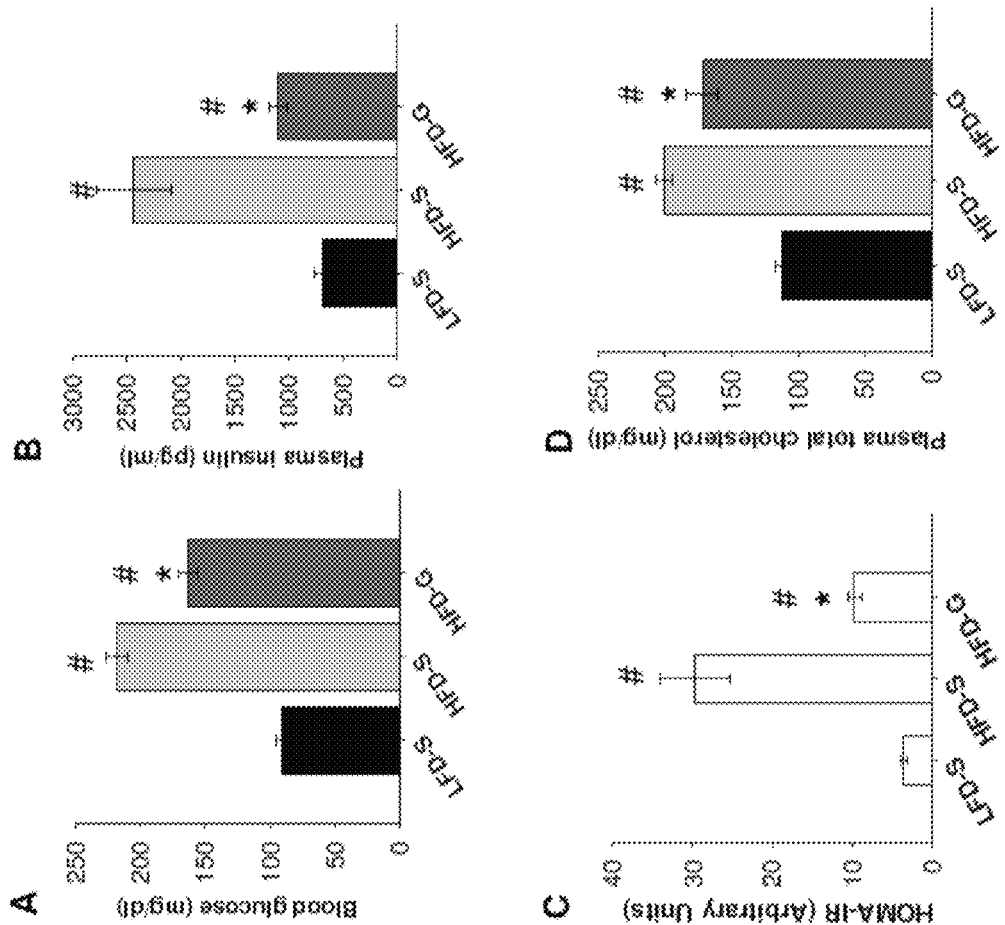
FIG. 6A through 6D are bar plots showing the measured levels of the indicated analytes in the bloodstream of mice under study.

Galantamine Lowers Fasting Blood Glucose and Plasma Insulin, Alleviates Insulin Resistance and Decreases Plasma Cholesterol Levels in High-fat Diet-fed Mice Significantly higher fasting blood glucose and plasma insulin levels was observed in the HFD-S mice as compared to LFD-S mice; galantamine significantly reduced these levels (HFD-G mice) (FIG. 6A and FIG. 6B). Applying the homeostatic model assessment insulin resistance (HOMA-IR) formula revealed increased insulin resistance in HFD-S mice as compared to the LFD-S group, and that galantamine reversed this insulin resistance (FIG. 6C). Plasma total cholesterol levels also were significantly elevated in the HFD-S mice as compared to the LFD-S mice and galantamine significantly decreased these levels in HFD-G mice (FIG. 6D). Together, these results indicate that galantamine significantly alleviates fasting hyperglycemia, hyperinsulinemia, insulin resistance and hypercholesterolemia.

Figure 11:
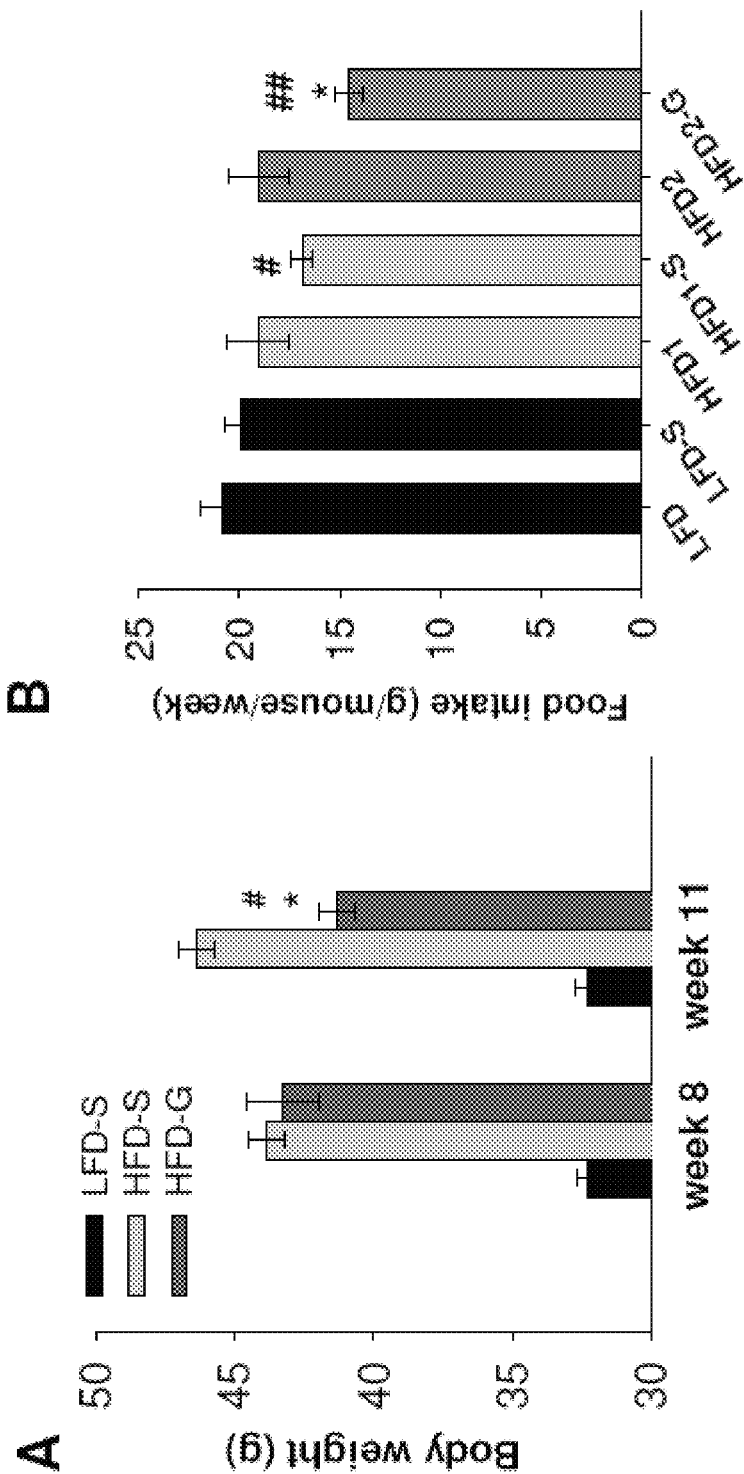
FIG. 11A and FIG. 11B are bar plots showing body weight and food intake of mice under study.

Galantamine Suppresses Body Weight Gain and Food Intake and Alleviates Impaired Insulin Sensitivity and Glucose Intolerance To further examine the effects of galantamine on obesity-related insulin resistance and impaired glucose homeostasis, in a separate experiment the same experimental design of high-fat diet-induced obesity was employed prior to subjecting mice to an insulin sensitivity test (IST) and a glucose tolerance test (GTT). As shown in FIG. 11A, at 8 weeks, the average body weight of mice on a high-fat diet was 11.25 g (P<0.05) higher than the body weight of mice on a low-fat diet. Importantly, while body weight of mice on the high-fat diet and treated with saline (HFD-S) continued to increase, the weight of mice on the high-fat diet and treated with galantamine (HFD-G) was decreased (FIG. 11A). Food intake suppression was statistically significant in the HFD-S and HFD-G groups of mice as compared to the prior to treatment values (FIG. 11B). In addition, the food intake in the galantamine-treated (HFD-G group) mice was significantly lower as compared to the HFD-S group of mice (FIG. 11B).

Figure 12:
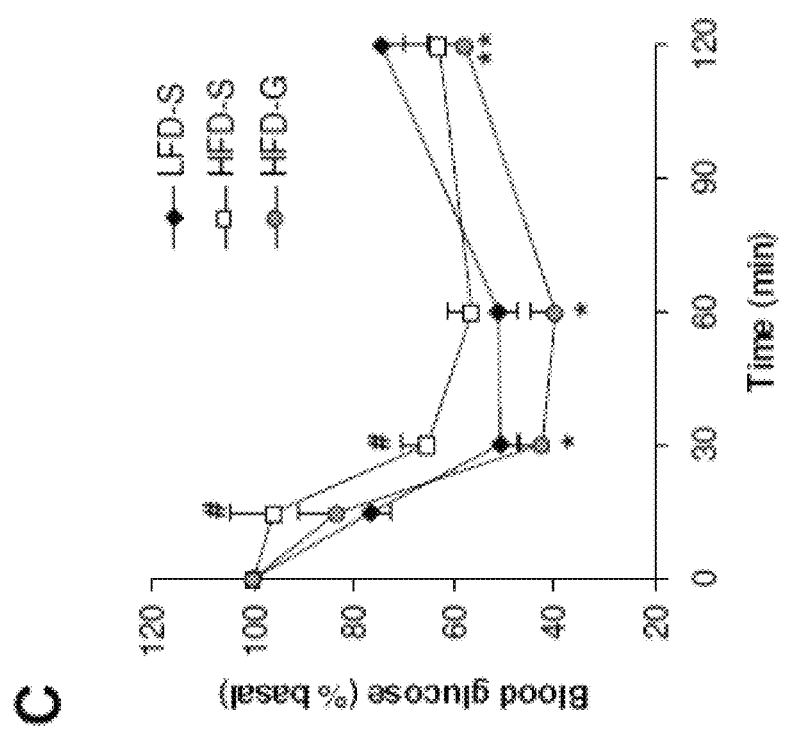
FIG. 12 is a plot showing blood glucose as a function of time during an IST test in the three groups of mice under study following insulin i.p. administration.

At the end of the 12 week experimental period mice were fasted overnight for IST and GTT. In the IST, following insulin i.p. administration, blood glucose in the LFD-S mice reached lowest levels at 30 min, and then increased, as determined at the 120 min time point (FIG. 12). Impaired insulin sensitivity in the HFD-S group of mice was indicated by higher blood glucose levels at the 15 min and 30 min time points as compared to the LFD-S mice (FIG. 12). Moreover, blood glucose in the HFD-S mice reached lower levels at 60 min, followed by no recovery upto the 120 min time point (FIG. 12). In contrast, blood glucose levels in the HFD-G mice decreased sharply to their lowest levels at 30 min, remained unchanged at 60 min, and increased at 120 min (FIG. 12). These values were significantly lower at 15 min and 30 min as compared to the HFD-S mice, and at 120 min, as compared to the LFD-S mice (FIG. 13).

Figures 13A, 13B:
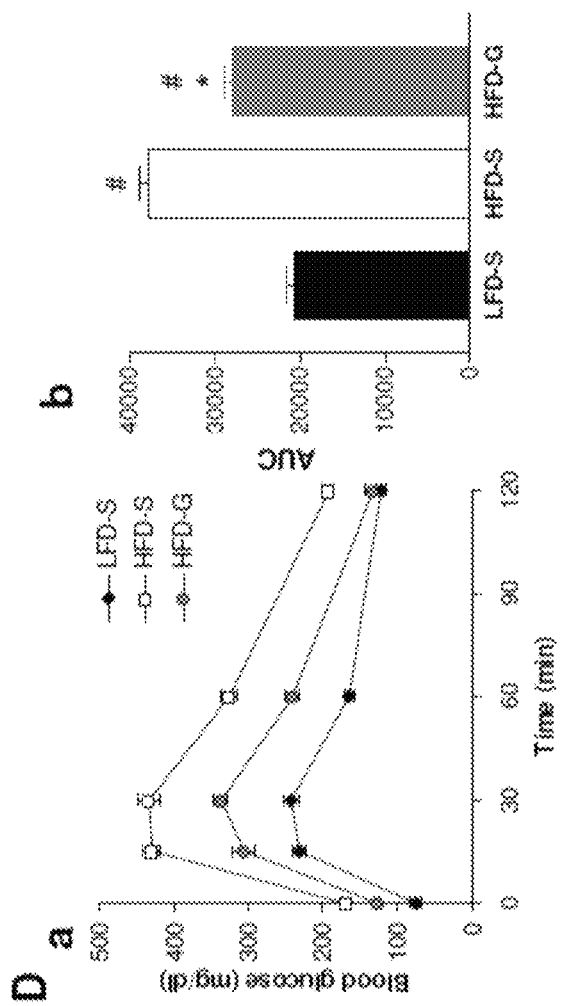
FIG. 13A is a plot showing blood glucose as a function of time during a GTT test in the three groups of mice under study.
FIG. 13B is a bar plot showing area under the curve shown in FIG. 13A.

In the GTT test the initial increase in blood glucose levels (after glucose administration) was higher in the HFD-S group of mice, as compared to the LFD-S group of mice (FIG. 13A). Galantamine treatment (HFD-G group) suppressed blood glucose levels as compared to the HFD-S group of mice (FIG. 13A). Accordingly, the area under the curve analysis of the GTT data showed higher values in the HFD-S mice as compared to the LFD-S mice (FIG. 13B), thus indicating increased (whole-body) insulin resistance. These values were significantly lower in the HFD-G mice as compared to the HFD-S mice (FIG. 13B). Together these results indicate that galantamine attenuates impaired insulin sensitivity, glucose intolerance and insulin resistance in high-fat diet-fed obese mice.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating a fatty liver disease in a subject in need thereof, comprising administering to the subject, as monotherapy, a pharmaceutical composition comprising an inert excipient, diluent, or carrier and an effective amount of a cholinergic pathway stimulating agent, wherein the fatty liver disease is selected from a non-alcoholic fatty liver (NAFL), alcoholic fatty liver (AFL), non-alcoholic steatohepatitis (NASH), alcoholic steatohepatitis (ASH), NASH-associated liver fibrosis, ASH-associated liver fibrosis, non-alcoholic cirrhosis and alcoholic cirrhosis.

2. The method of claim 1, wherein the fatty liver disease is alcoholic fatty liver (AFL).

3. The method of claim 1, wherein the fatty liver disease is alcoholic steatohepatitis (ASH).

4. The method of claim 1, wherein the cholinergic pathway stimulating agent is selected from the group consisting of a nicotinic receptor agonist, a muscarinic receptor agonist, a cholinesterase inhibitor and an antagonist of presynaptic acetylcholine autoreceptors.

5. The method of claim 4, wherein the cholinergic pathway stimulating agent is a cholinesterase inhibitor selected from the group consisting of galantamine, tacrine, fasciculin, metrifonate, heptyl-physostigmine, norpyridostigmine, norneostigmine, huperzine A, physostigmine, velnacrine, citicoline, donepizil, 7-methoxytacrine, eptastigmine, icopezil, ipidacrine, zifrosilone, anseculin, suronacrine, linopiridine, rivastigmine, neostigmine, edrophonium, demacarium, ambenonium, arecoline, xanomeline, subcomeline, cevimeline, alvameline, milameline, talsaclidine, and compounds of the following structural formulae:

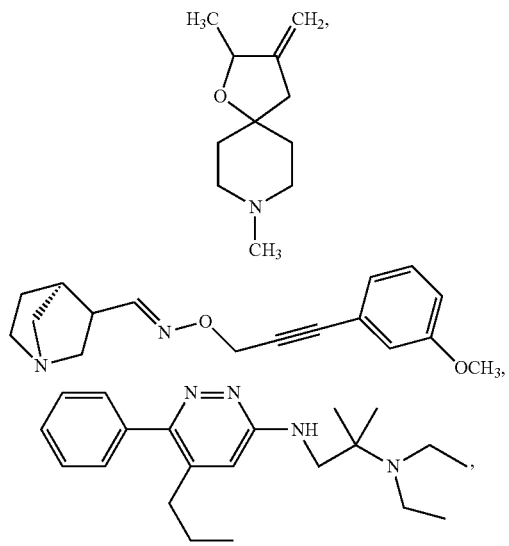

-continued

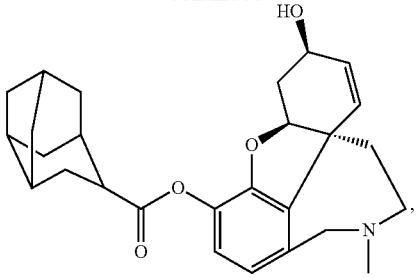

or a pharmaceutically acceptable salt thereof.

6. The method of claim 5, wherein the cholinesterase inhibitor is galantamine.

7. The method of claim 4, wherein the cholinergic pathway stimulating agent is a nicotinic receptor agonist.

8. The method of claim 7, wherein the nicotinic receptor agonist is a compound of structural formula (III):

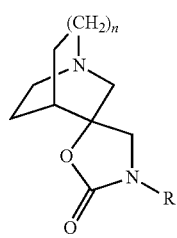

(III)

wherein:
R is hydrogen or methyl; and
n is 0 or 1; or
a pharmaceutically acceptable salt thereof.

9. The method of claim 8, wherein the nicotinic receptor agonist is (−)-spiro-[1-azabicyclo[2.2.2]octane-3,5'-octane-3,5'oxazolidin-2'-one].

10. The method of claim 7, wherein the nicotinic receptor agonist is a compound of structural formula (IV):

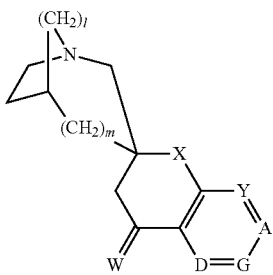

(IV)

wherein:
l is 1 or 2;
m is 0 or 1;
Y is CH, N, or NO;
X is oxygen or sulfur;
W is oxygen, $H_2$, or $F_2$;
A is N or $C(R^2)$;
G is N or $C(R^3)$;
D is N or $C(R^4)$;
$R^2$, $R^3$, and $R^4$ are independently hydrogen, halogen, $C_1$-$C_4$ alkyl, $C_2$-$C_4$ alkenyl, $C_2$-$C_4$ alkynyl, aryl, heteroaryl, OH, $OC_1$-$C_4$ alkyl, $CO_2R^1$, —CN, —$NO_2$, —$NR^5R^6$, —$CF_3$ or —$OSO_2CF_3$; or $R^2$ and $R^3$, or $R^3$ and $R^4$, respectively, may together form another six membered aromatic or heteroaromatic ring sharing A and G, or G and D, respectively, containing between zero and two nitrogen atoms, and substituted with one to two of the following substitutents: independently hydrogen, halogen, $C_1$-$C_4$ alkyl, $C_2$-$C_4$ alkenyl, $C_2$-$C_4$ alkynyl, aryl, heteroaryl, OH, $OC_1$-$C_4$ alkyl, $CO_2R^{1'}$, —CN, —$NO_2$, —$NR^{5'}R^{6'}$, —$CF_3$ or —$OSO_2CF_3$;

$R^1$ and $R^{1'}$ are independently hydrogen or $C_1$ to $C_4$ alkyl;

$R^5$, $R^{5'}$, $R^6$ and $R^{6'}$ are independently hydrogen, $C_1$-$C_4$ alkyl, $C(O)R^7$, $C(O)NHR^8$, $C(O)OR^9$, $SO_2R^{10}$ or may together be $(CH_2)_jQ(CH_2)_k$; where Q is O, S, $NR^{11}$, or a bond;

j is 2 to 7; and k is 0 to 2; and $R^7$, $R^8$, $R^9$, $R^{10}$, and $R^{11}$ are independently $C_1$-$C_4$, alkyl, aryl, or heteroaryl, an enantiomer thereof, or a pharmaceutically acceptable salt thereof.

11. The method of claim 10 wherein the nicotinic receptor agonist is (R)-(−)-5'-phenylspiro[1-azabicyclo[2.2.2]octane-3,2'octane-3,2'(3'H)-furo[2,3-b]pyridine].

12. The method of claim 7, wherein the nicotinic receptor agonist is a compound of structural formula (V):

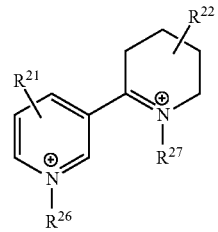

(V)

wherein:
$R^{21}$ is hydrogen or $C_1$-$C_4$ alkyl, $R^{26}$, and $R^{27}$ are independently selected from hydrogen, or $C_1$-$C_4$ alkyl or may be absent; and $R^{22}$ is:

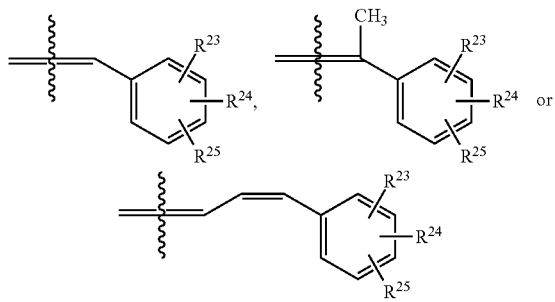

wherein:
$R^{23}$, $R^{24}$ and $R^{25}$ are independently hydrogen, $C_1$-$C_4$ alkyl optionally substituted with N,N-dialkylamino having 1 to 4 carbons in each of the alkyls, $C_1$-$C_6$ alkoxy optionally substituted with N, N-dialkylamino having 1 to 4 carbons in each of the alkyls, carboalkoxy having 1 to 4 carbons in the alkoxy, amino, amido having 1 to 4 carbons in the acyl, cyano, and N,N-dialkylamino having 1 to 4 carbons in each of the alkyls, halo, hydroxyl, or nitro.

13. The method of claim 12 wherein the nicotinic receptor agonist is 3-(4-hydroxy-2-methoxybenzylidene)anabaseine.

14. The method of claim 12, wherein the nicotinic receptor agonist is 3-(2,4-dimethoxybenzylidene)anabaseine (DMXB-A).

15. The method of claim 7, wherein the nicotinic receptor agonist is (1-aza-bicyclo [2.2.2]oct-3-yl)-carbamic acid 1-(2-fluorophenyl)-ethyl ester.

16. The method of claim 7, wherein the nicotinic receptor agonist is cocaine methiodide.

17. The method of claim 7, wherein the nicotinic receptor agonist is choline.

18. The method of claim 7, wherein the nicotinic receptor agonist is a compound of structural formula (VI):

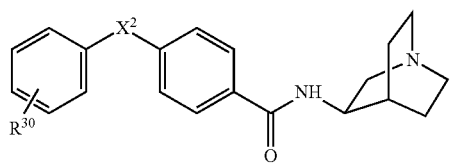

(VI)

wherein:
$X^2$ is O or S;
$R^{30}$ is H, $OR^{31}$, $NHC(O)R^{31}$, or a halogen; and
$R^{31}$ is a $C_1$-$C_4$ alkyl; or
a pharmaceutically acceptable salt thereof.

19. The method of claim 4, wherein the cholinergic pathway stimulating agent is a muscarinic receptor agonist.

20. The method of claim 19, wherein the muscarinic receptor agonist is muscarine, McN-A-343, or MT-3.

21. The method of claim 19, wherein the muscarinic receptor agonist is an aromatic amidinohydrazone.

22. The method of claim 21, wherein the muscarinic receptor agonist is a compound having the structural formula (I):

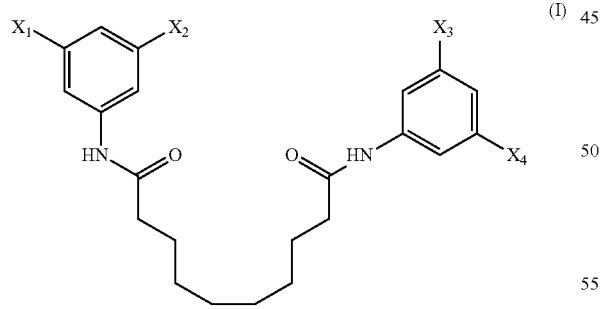

(I)

wherein
$X_1$, $X_2$, $X_3$ and $X_4$ is each independently GhyCH, GhyCCH$_3$, redGhyCH$_2$, or redGhyCHCH$_3$, or H, provided at least one of $X_1$, $X_2$, $X_3$ and $X_4$ is not H,
wherein GhyCH is NH$_2$(CNH)—NH—N=CH—, GhyCCH$_3$ is NH$_2$(CNH)—NH—N=C(CH$_3$)—, redGhyCH$_2$ is NH$_2$(CNH)—NH—NH—CH$_2$— and redGhyCHCH$_3$ is NH$_2$(CNH)—NH—NH—CH(CH$_3$)—,
or a pharmaceutically acceptable salt thereof.

23. The method of claim 21, wherein the muscarinic agonist is N,N'-bis(3,5-diacetylphenyl) decanediamide tetrakis (amidinohydrazone) tetrahydrochloride (CNI-1493).

24. The method of claim 1, wherein the cholinergic pathway stimulating agents is an antagonist of a presynaptic acetylcholine autoreceptor.

25. The method of claim 24, wherein the antagonist of a presynaptic acetylcholine autoreceptor is selected from

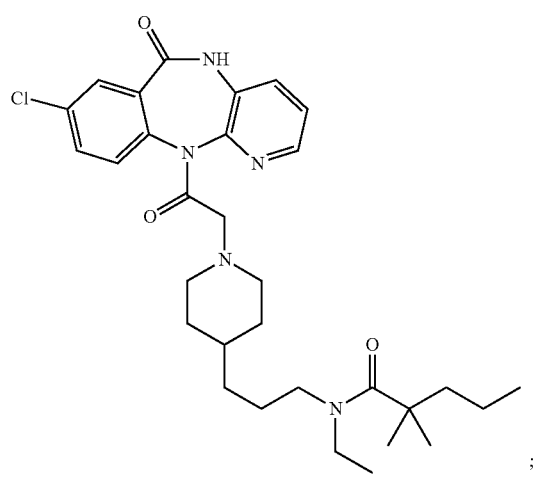

;

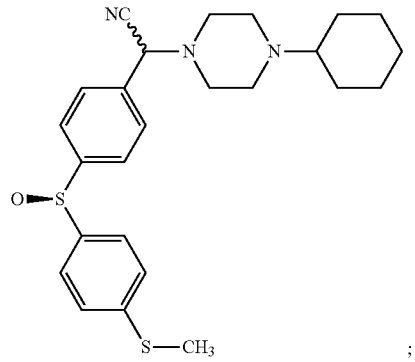

;

-continued

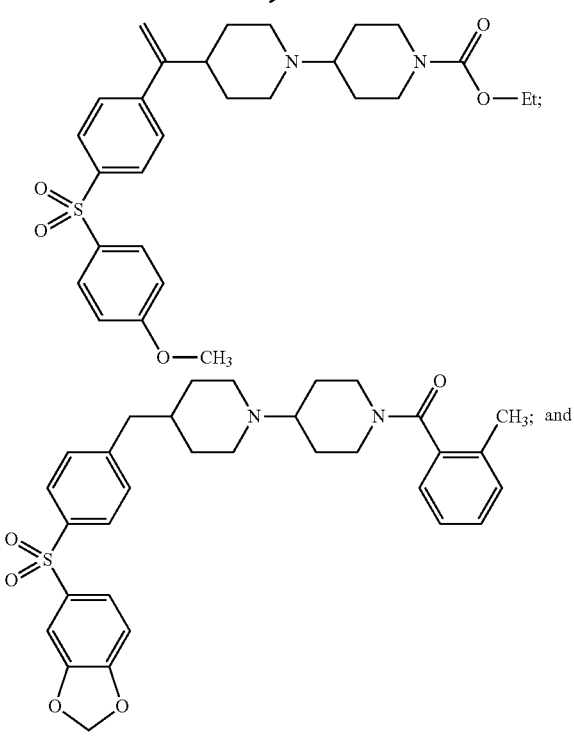

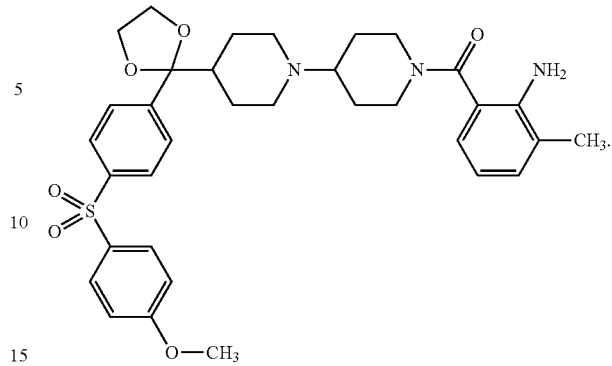

26. The method of claim 1, wherein the subject does not have diabetes.

27. The method of claim 1, wherein the fatty liver disease is non-alcoholic fatty liver (NAFL).

28. The method of claim 1, wherein the fatty liver disease is non-alcoholic steatohepatitis (NASH).

29. The method of claim 1, wherein the fatty liver disease is selected from NASH-associated liver fibrosis and ASH-associated liver fibrosis.

* * * * *

UNITED STATES PATENT AND TRADEMARK OFFICE
CERTIFICATE OF CORRECTION

PATENT NO. : 8,865,641 B2  Page 1 of 1
APPLICATION NO. : 13/523519
DATED : October 21, 2014
INVENTOR(S) : Valentin A. Pavlov et al.

It is certified that error appears in the above-identified patent and that said Letters Patent is hereby corrected as shown below:

In the Claims

Column 34, Claim 25, lines 50-65. Please delete " 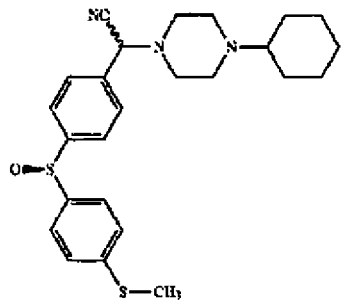 :" and insert -- 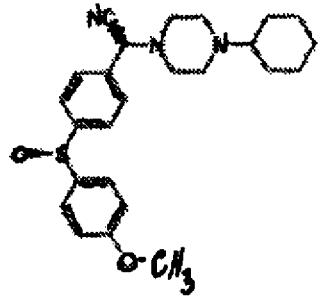 ;--

Signed and Sealed this
Tenth Day of February, 2015

Michelle K. Lee
*Deputy Director of the United States Patent and Trademark Office*